United States Patent
Epstein et al.

[19]

[11] Patent Number: 6,045,570
[45] Date of Patent: Apr. 4, 2000

[54] BIOLOGICAL SEALANT MIXTURE AND SYSTEM FOR USE IN PERCUTANEOUS OCCLUSION OF PUNCTURE SITES AND TRACTS IN THE HUMAN BODY AND METHOD

[75] Inventors: Gordon H. Epstein, Fremont; Todd E. Lempert, Piedmont; Brian B. Martin, Boulder Creek, all of Calif.

[73] Assignee: Biointerventional Corporation, Pleasanton, Calif.

[21] Appl. No.: 09/161,193

[22] Filed: Sep. 25, 1998

Related U.S. Application Data

[63] Continuation-in-part of application No. 09/126,963, Jul. 31, 1998, which is a continuation-in-part of application No. 08/972,383, Nov. 18, 1997, Pat. No. 5,922,009, which is a continuation-in-part of application No. 08/798,860, Feb. 11, 1997, Pat. No. 5,782,860.

[51] Int. Cl.[7] .................................................... A61K 17/08
[52] U.S. Cl. ............................................................. 606/214
[58] Field of Search ..................... 606/214, 213, 606/215, 216; 604/60, 168, 52; 424/448, 443

[56] References Cited

U.S. PATENT DOCUMENTS

| | | | |
|---|---|---|---|
| 4,061,731 | 12/1977 | Gottlieb | 424/448 |
| 4,600,574 | 7/1986 | Lindner et al. | 424/448 |
| 5,258,000 | 11/1993 | Gianturco | 606/151 |
| 5,282,827 | 2/1994 | Kensey et al. . | |
| 5,290,552 | 3/1994 | Sierra et al. | 424/448 |
| 5,549,633 | 8/1996 | Evans et al. . | |
| 5,591,204 | 1/1997 | Janzen et al. . | |
| 5,626,601 | 5/1997 | Gershony et al. . | |
| 5,838,896 | 1/1995 | Gershony et al. | 606/213 |

OTHER PUBLICATIONS

Oct. 19, 1999, PCT Search Report, US99/17367.
Oct.29, 1999, PCT Search Report, US99/17372.

*Primary Examiner*—Michael Buiz
*Assistant Examiner*—Vikki Trinh
*Attorney, Agent, or Firm*—Flehr Hohbach Test Albritton & Herbert

[57] ABSTRACT

A biological sealant comprising a gelatin slurry. The slurry contains gelatin, saline or water and thrombin.

42 Claims, 17 Drawing Sheets

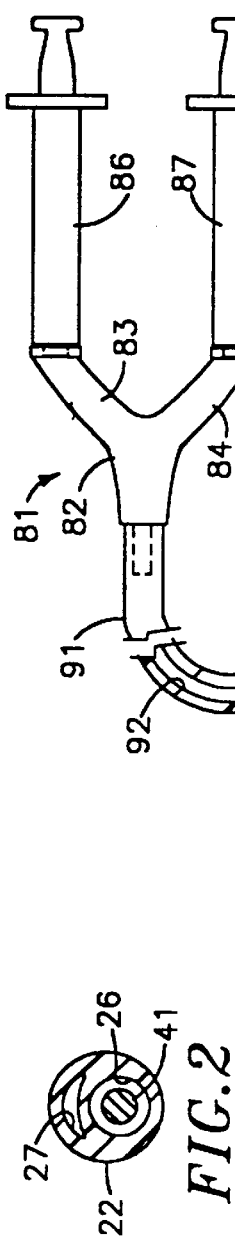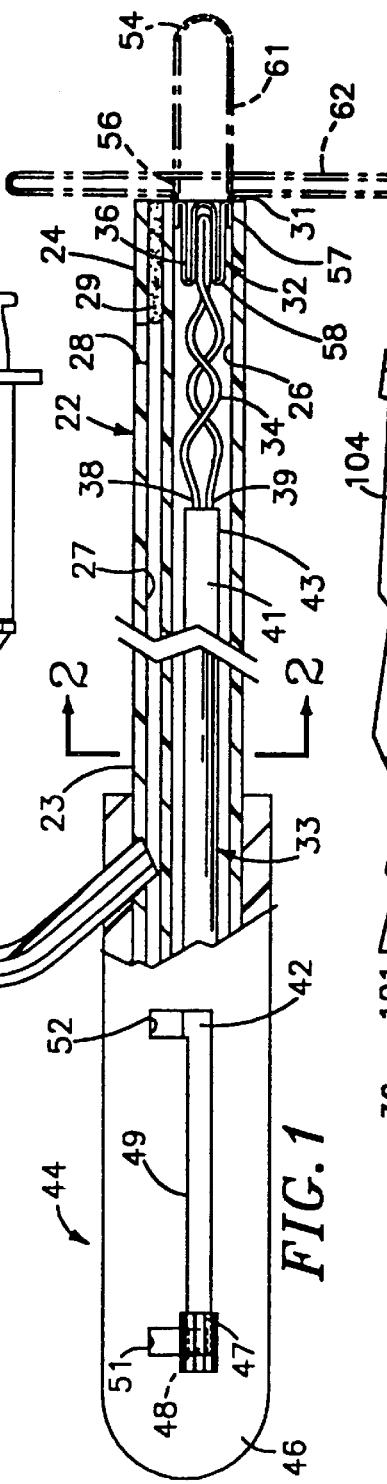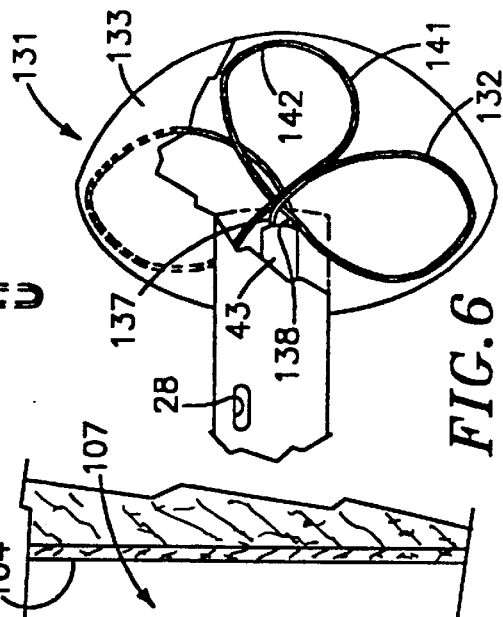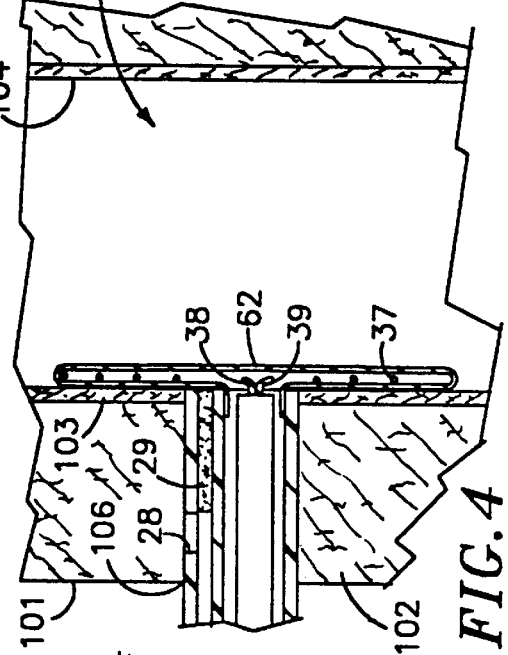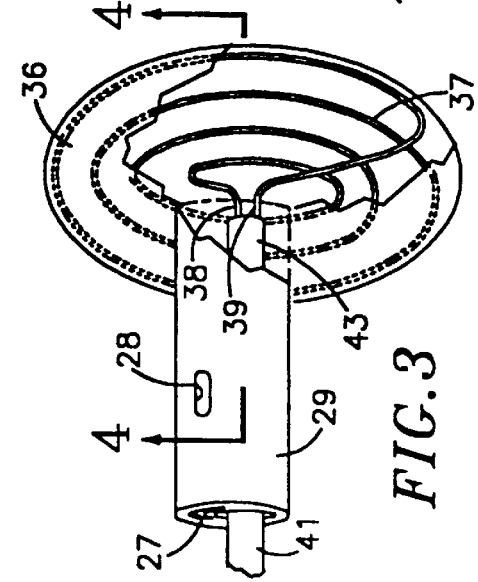

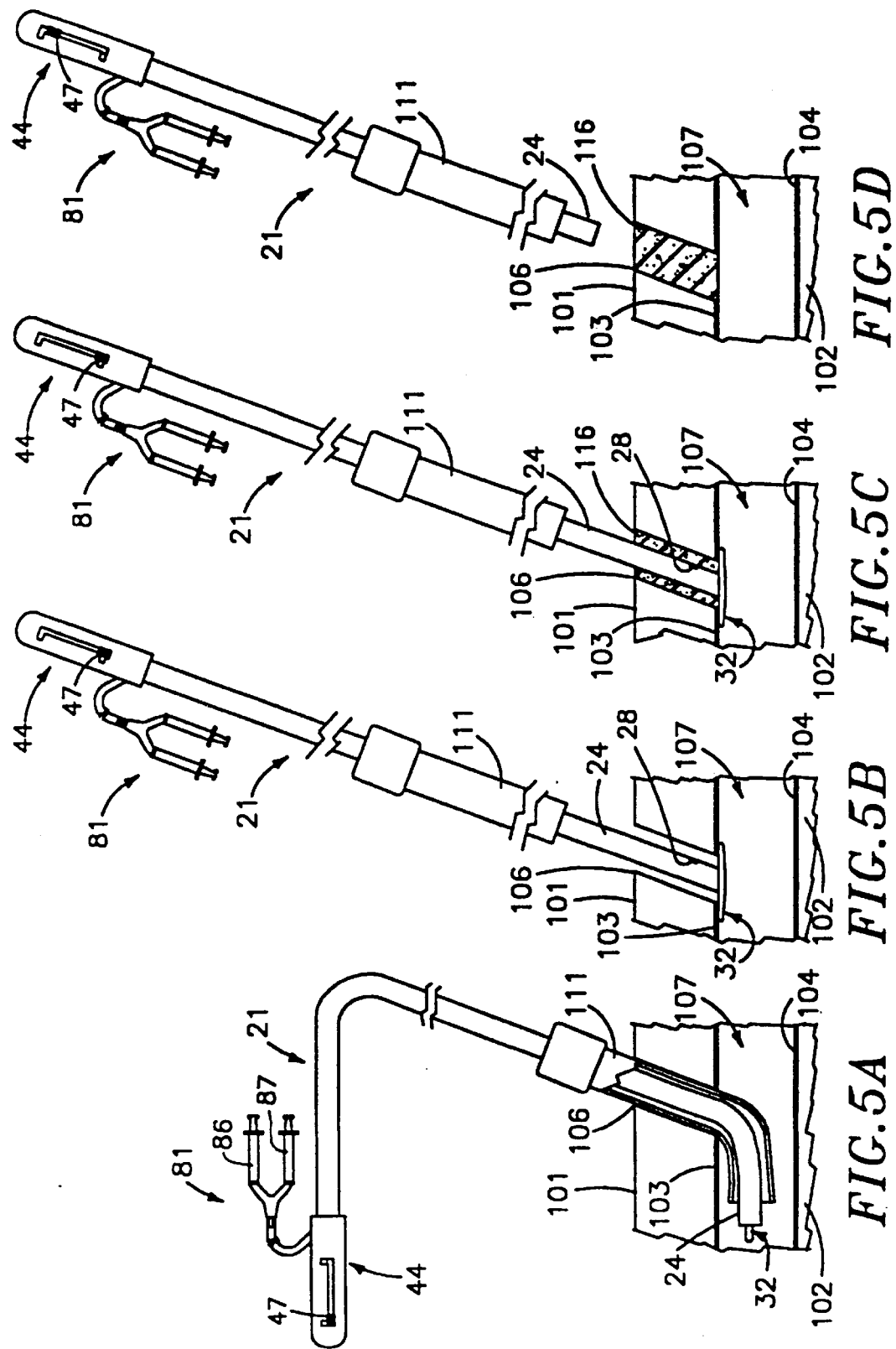

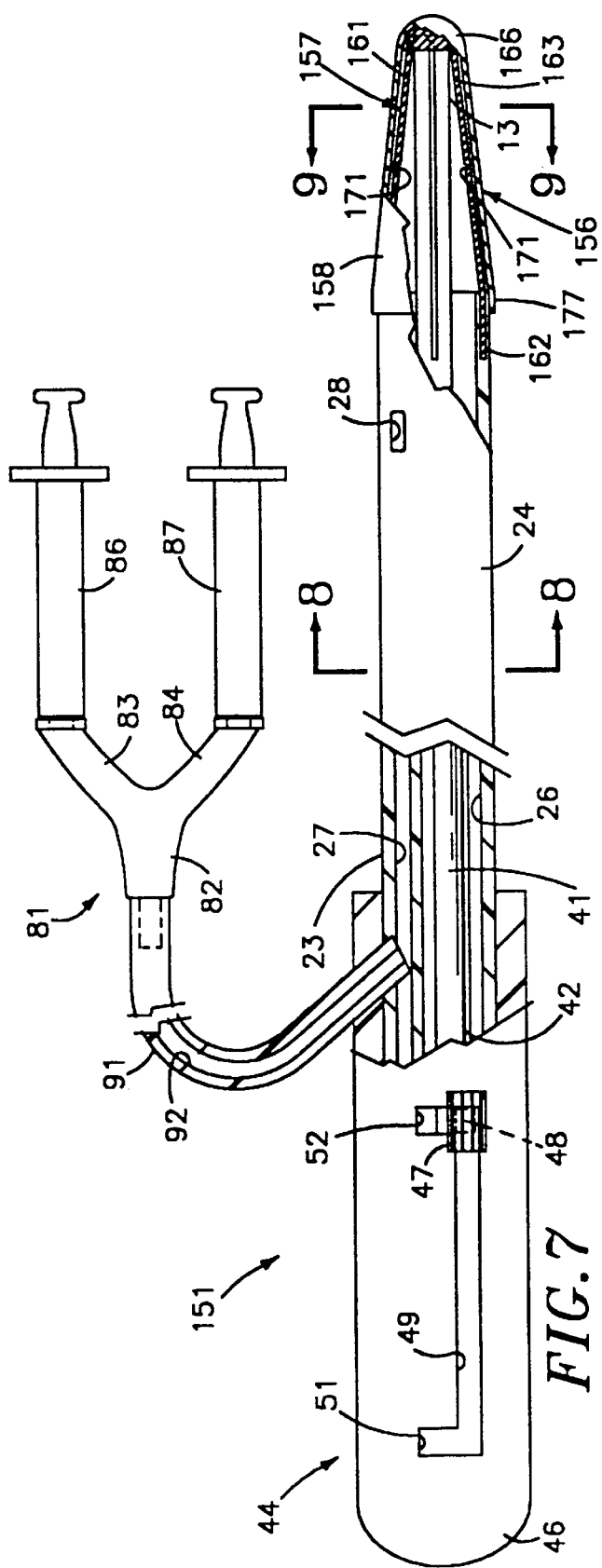
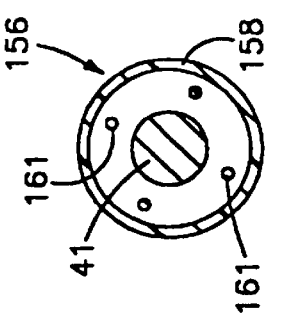
FIG. 9
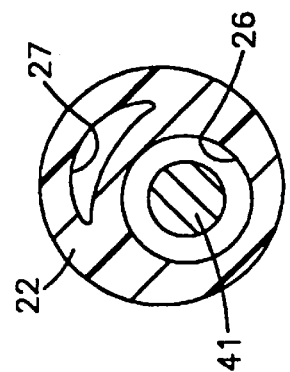
FIG. 8
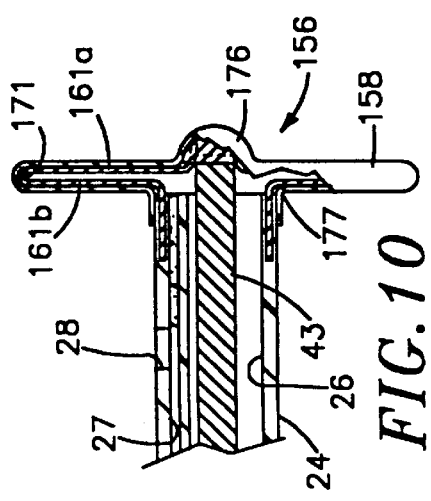
FIG. 10
FIG. 7

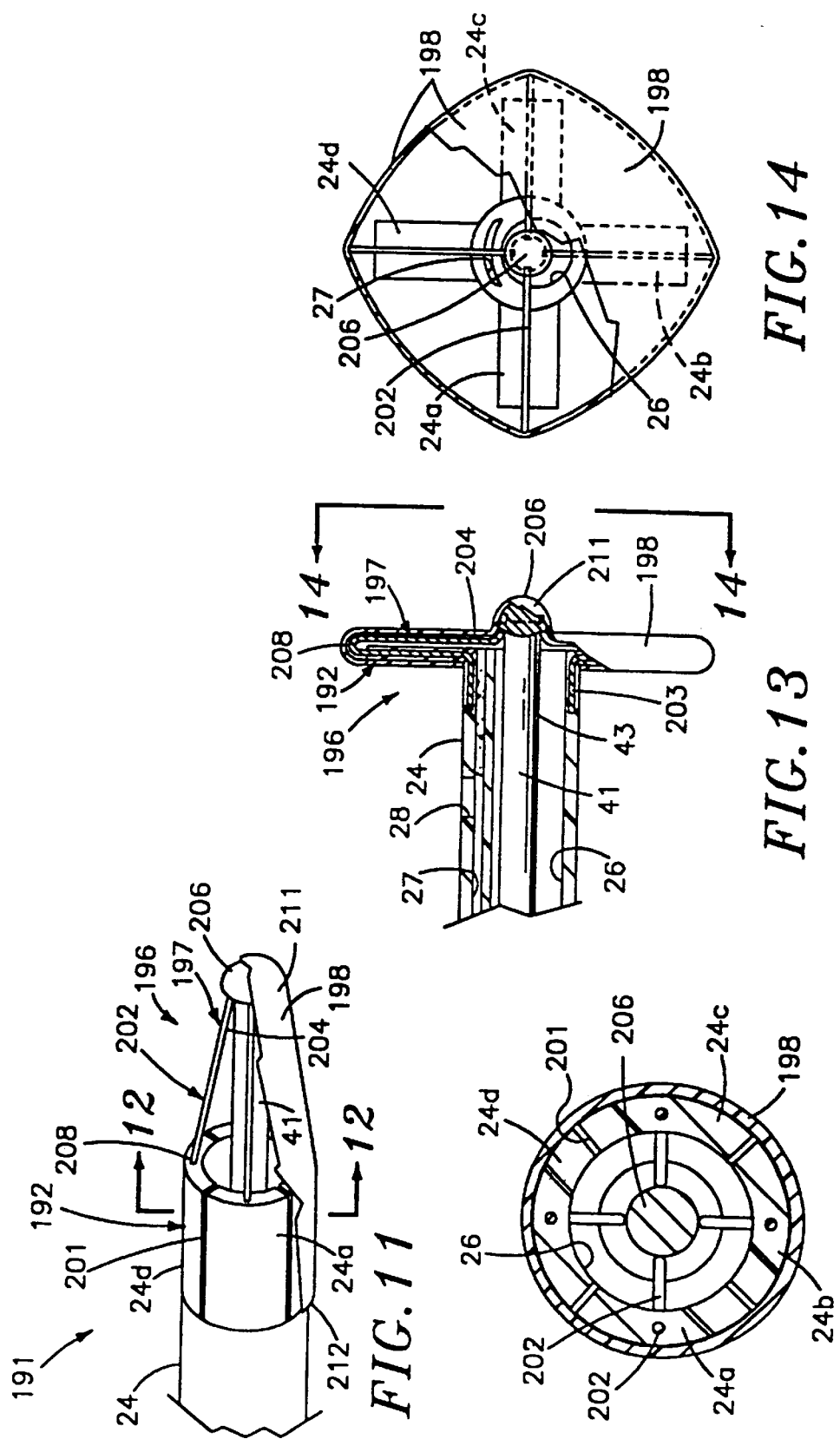

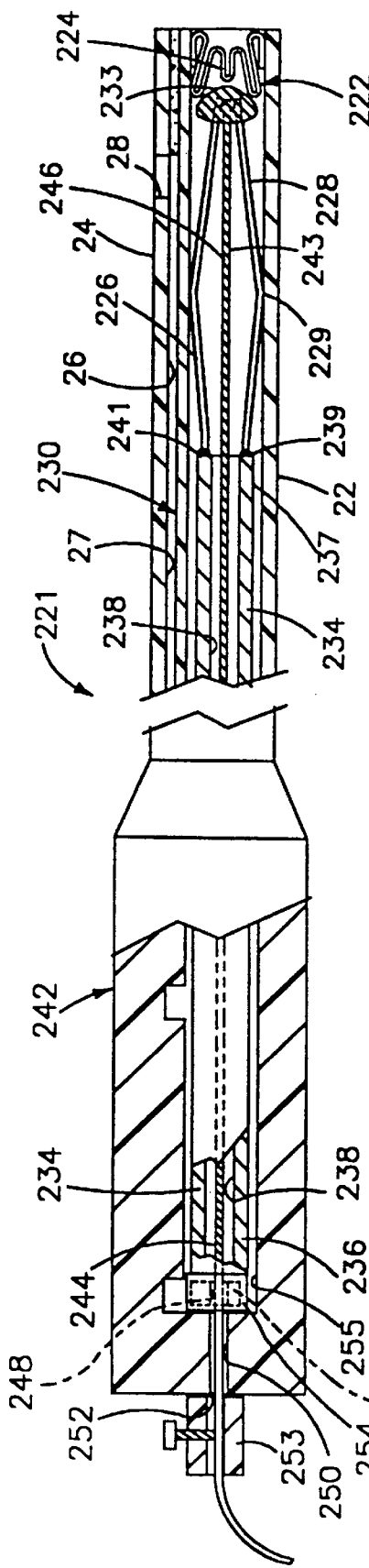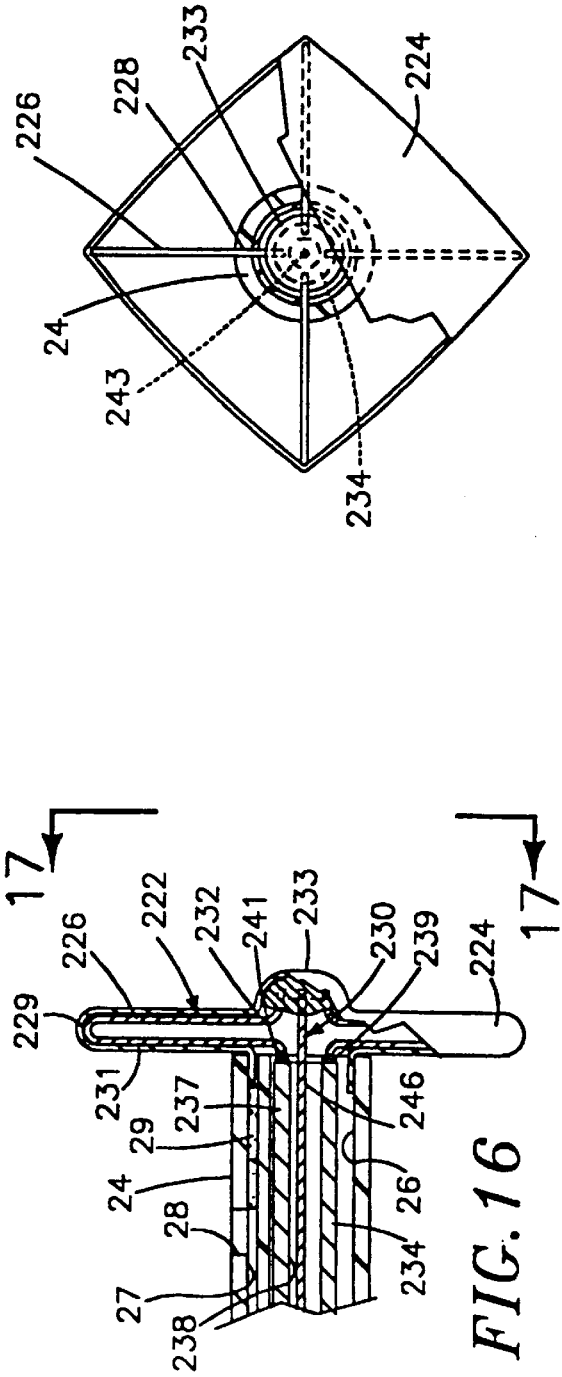

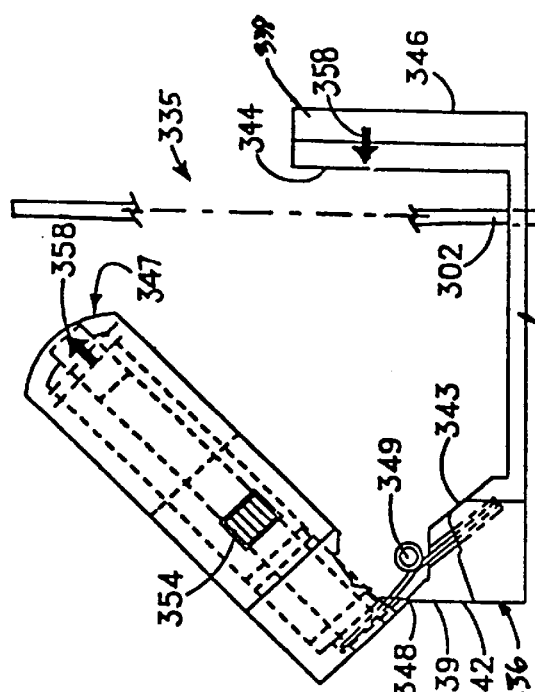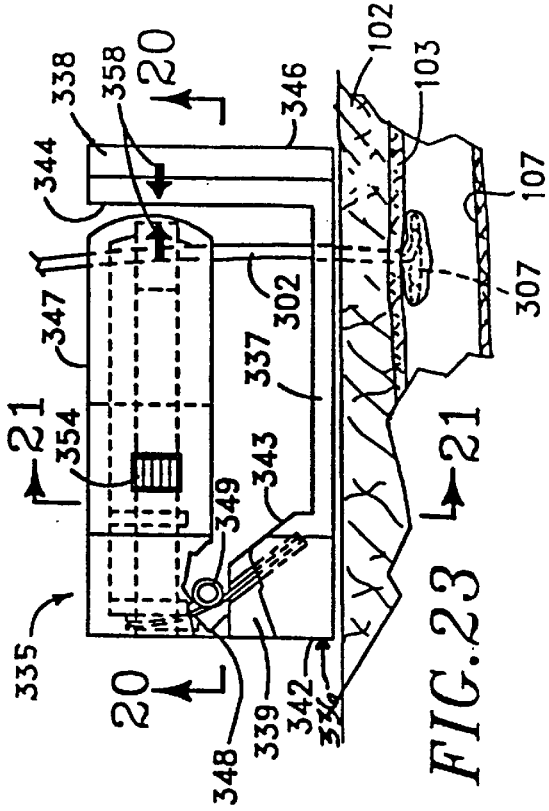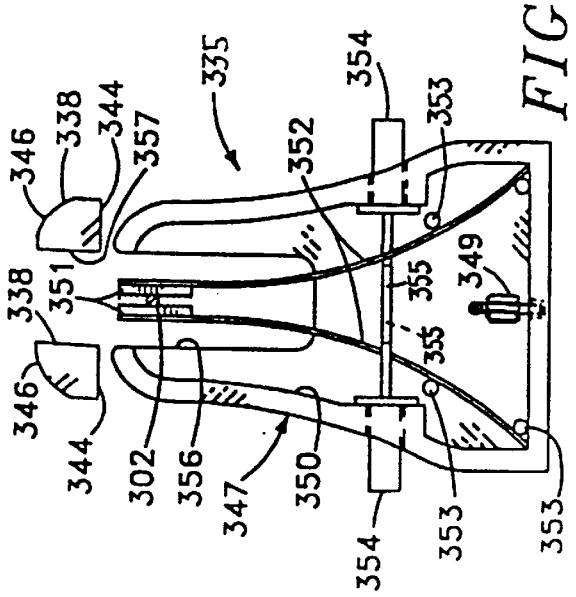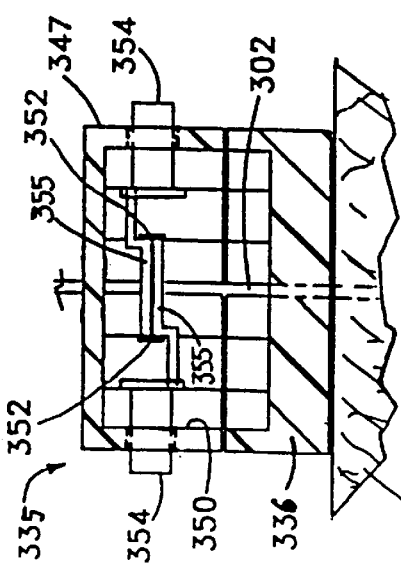

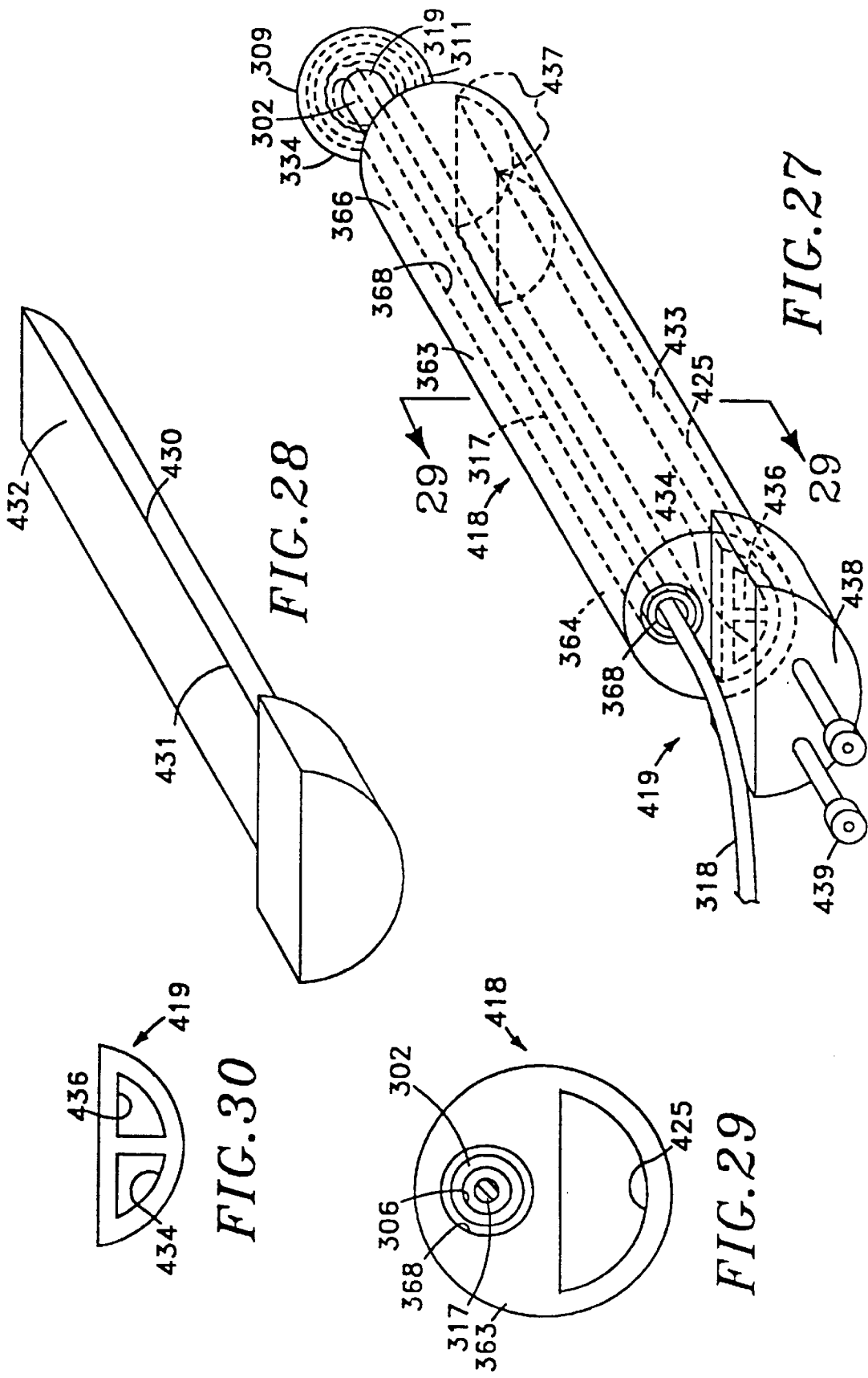

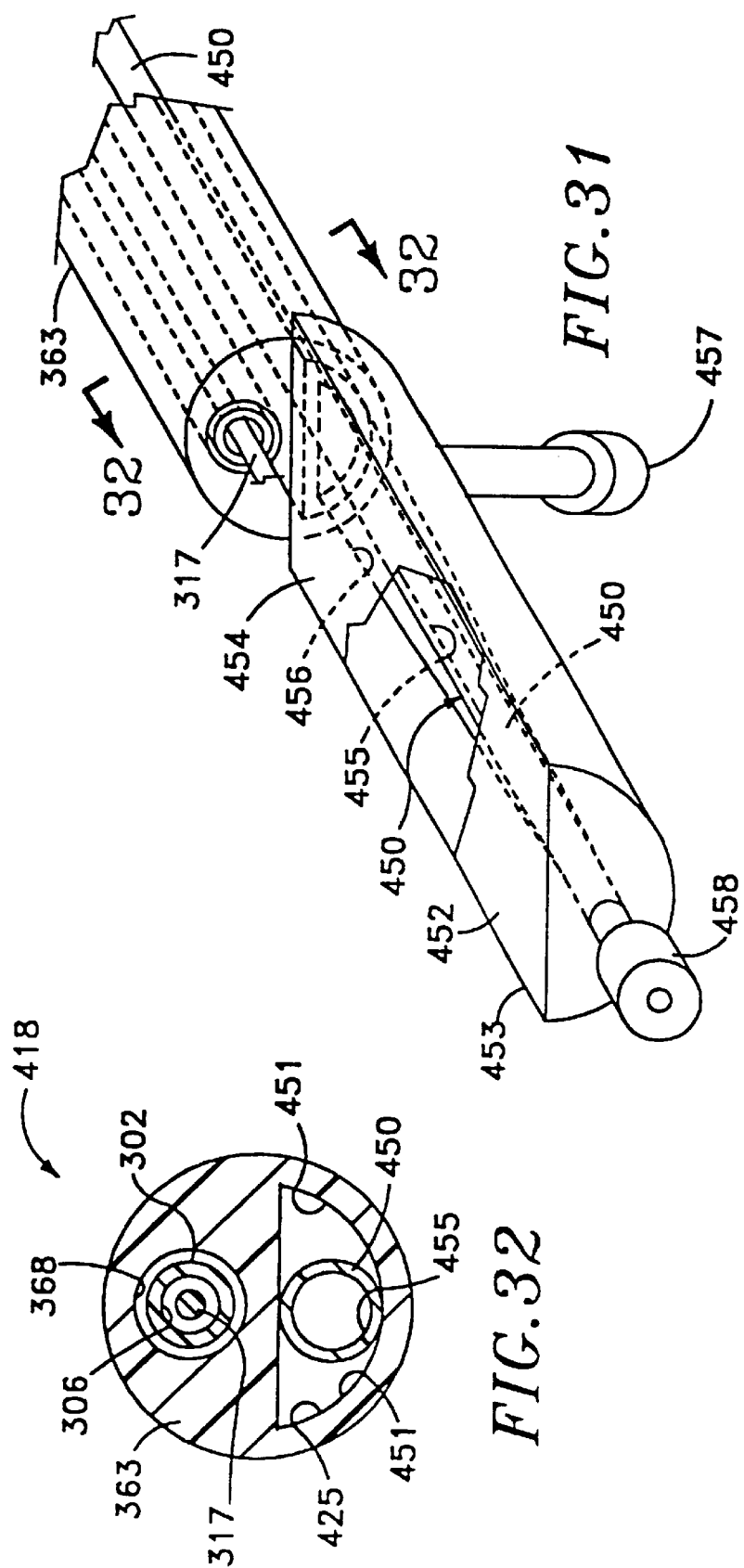

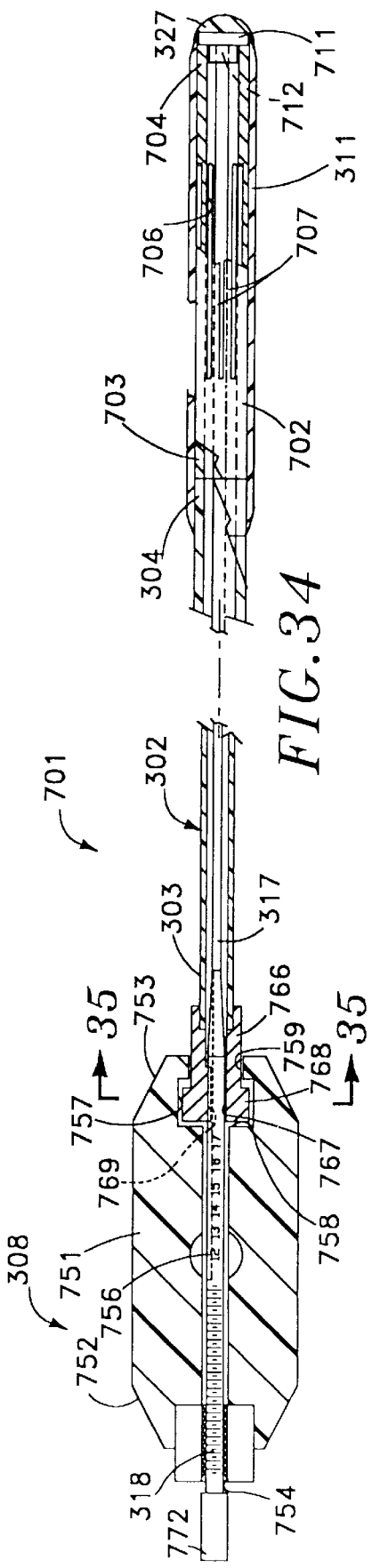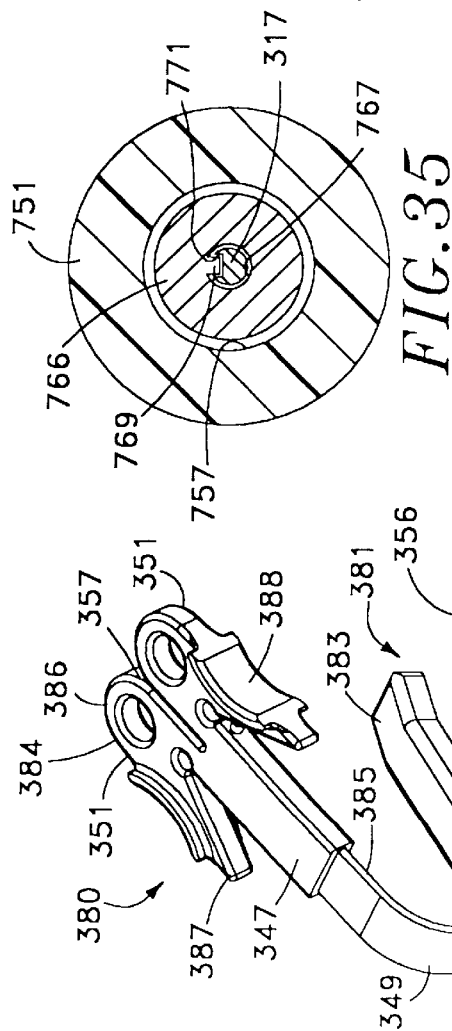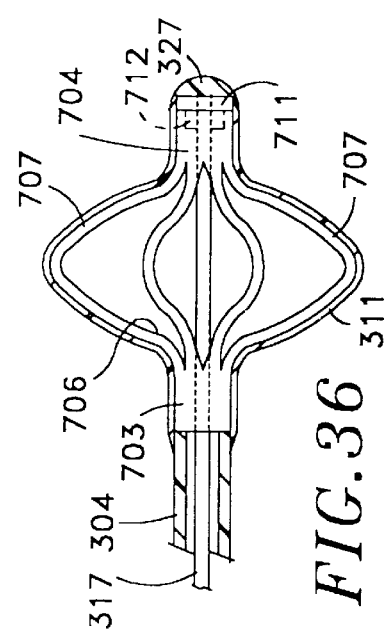

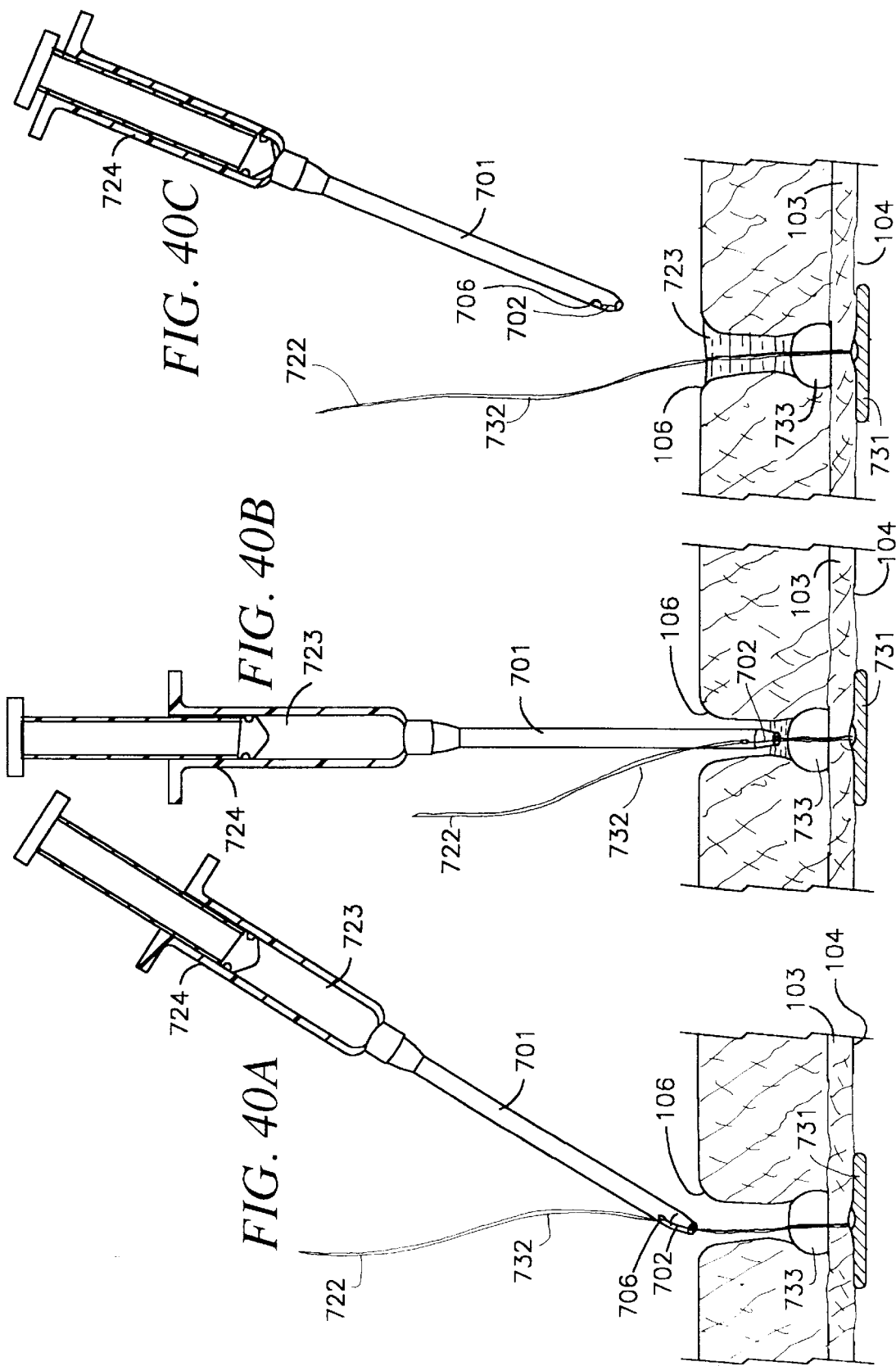

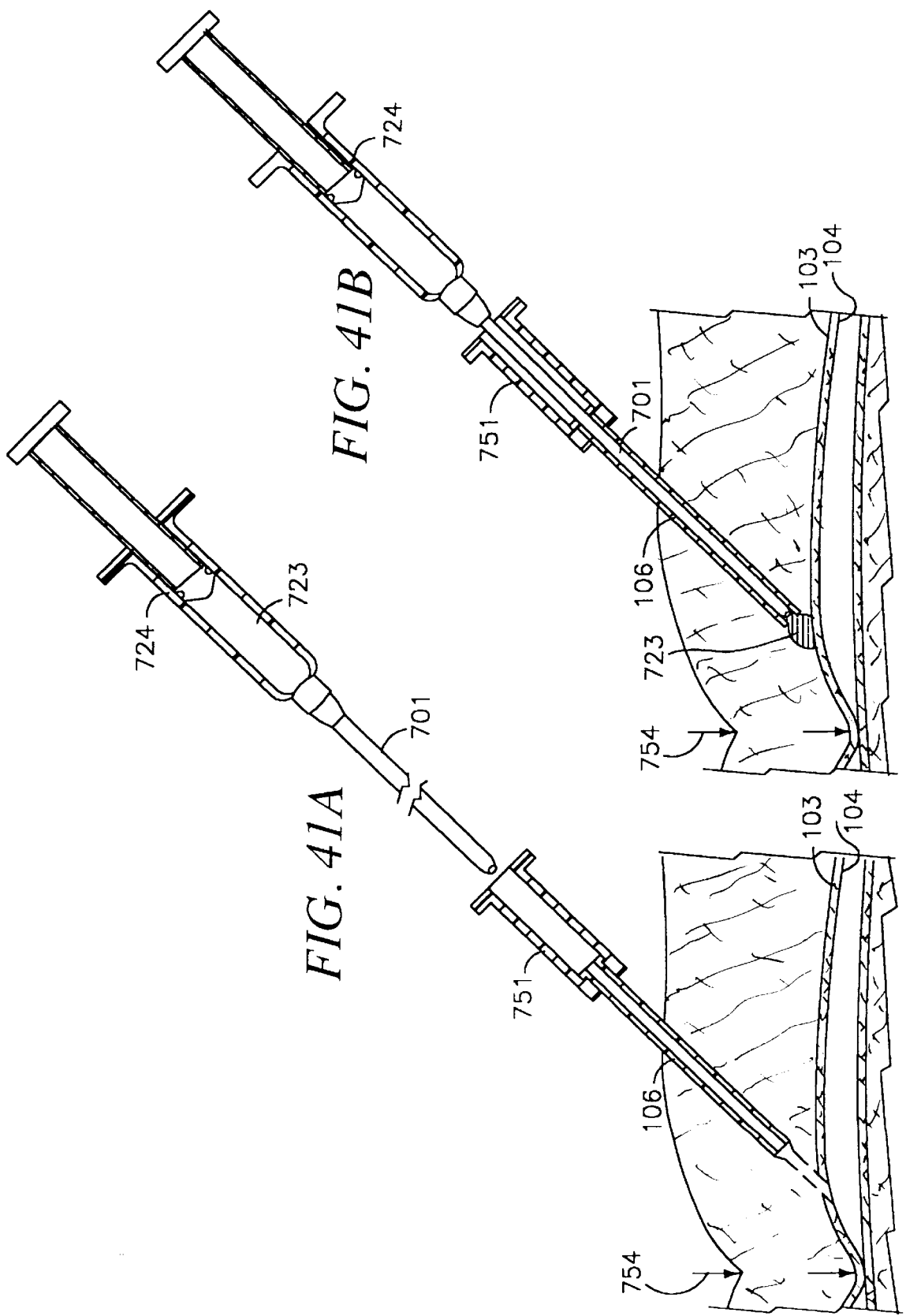

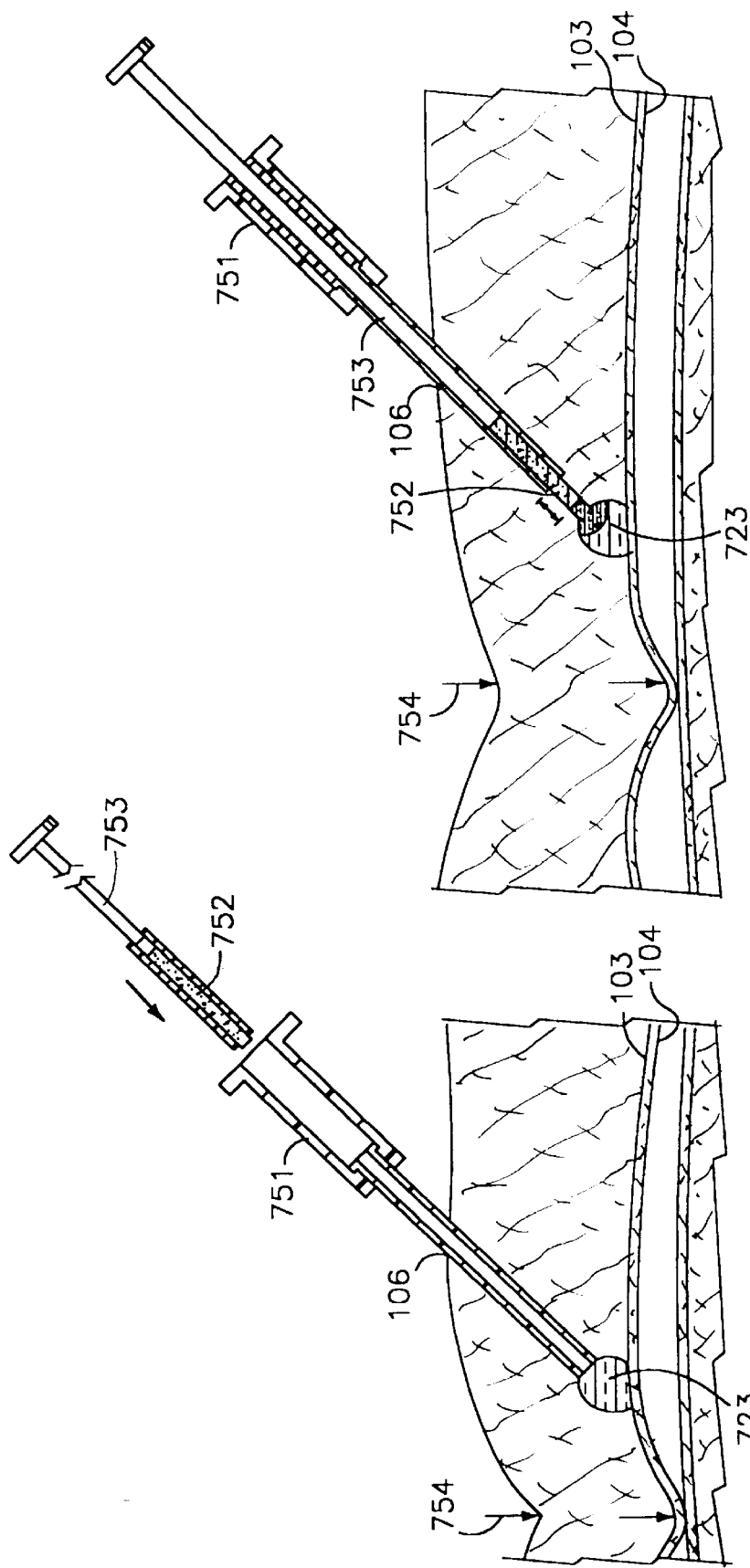

BIOLOGICAL SEALANT MIXTURE AND SYSTEM FOR USE IN PERCUTANEOUS OCCLUSION OF PUNCTURE SITES AND TRACTS IN THE HUMAN BODY AND METHOD

This is a continuation-in-part of prior application Ser. No. 09/126,963 filed Jul. 31, 1998 which is a continuation-in-part of application Ser. No. 08/972,383, filed Nov. 18, 1997 now U.S. Pat. No. 5,922,009 which is a continuation-in-part of application Ser. No. 08/798,870, filed Feb. 11, 1997 which issued as U.S. Pat. No. 5,782,860 on Jul. 21, 1998.

This invention relates to an expansile device and tension application device for use therewith, for use in vascular and non-vascular tracts in the human body and method and more particularly for percutaneous occlusion of vascular access sites in the human body.

Percutaneous access to the blood vessels and organs of the human body for diagnosis and treatment of disease processes has heretofore been accomplished. Percutaneous vascular procedures are performed involving the coronary, peripheral and cerebral vasculature. These procedures include coronary and peripheral angiography, angioplasty, atherectomies, coronary retroperfusion and retroinfusion, cerebral angiograms, treatment of strokes, cerebral aneurysms and the like. Patients undergoing such procedures are often treated with anti-platelet drugs, anticoagulants such as heparin, thrombolytics, or a combination thereof, all of which interfere with coagulation making it more difficult for the body to seal a puncture site. Various devices and methods have heretofore been utilized, however, they all have had deficiencies, including the use of complicated devices and methods. In addition, difficulties are still encountered in obtaining good seals. There is therefore a need for a device and method for percutaneous access and occlusion of vascular access sites and other puncture sites and natural tracts in the human body which overcome the deficiencies of prior art devices and methods.

In general, it is an object of the present invention to provide a closure device and method for percutaneous access and occlusion of vascular access sites, other puncture sites and natural tracts in the human body which will make possible a positive seal of the puncture site or tract promoting rapid healing of the puncture site or tract.

Another object of the invention is to provide a closure device and method of the above character which can be easily and reliably used.

Another object of the invention is to provide a closure device and method of the above character in conjunction with which a biological sealant is used by introduction into the puncture site or natural tract.

Another object of the invention is to provide a closure device and method of the above character which leaves a small enough opening after removal of the closure device so that the biological sealant will seal the remaining opening.

Another object of the invention is to provide a closure device and method of the above character which enables continued substantially unobstructed blood flow during deployment and use of the closure device.

Another object of the invention is to provide a closure device and method of the above character in which no foreign body remains in the blood vessel.

Another object of the invention is to provide a closure device and method of the above character that permits early ambulation of patients and avoids prolonged bed rest.

Another object of the invention is to provide a closure device and method of the above character which reduces the risk of bleeding, formation of arteriovenous fistula, formation of pseudoaneurysm, thrombosis with distal embolization and infection.

Another object of the invention is to provide a closure device and method of the above character that reduces the risk of causing ischemia of an extremity.

Another object of the invention is to provide a closure device and method of the above character that is inexpensive, quick, safe, easy to use and is disposable.

Another object of the invention is to provide an expansile device and method of the above character in which the configuration of an expansile assembly is determined by countervailing mechanical forces of an expansile member and a membrane.

Another object of the invention is to provide an expansile device and method of the above character in which tensioning means is provided for reversibly maintaining engagement of the expansile assembly against the vessel wall of a puncture and to free the operator's hands from having to hold the device after it is correctly deployed in the puncture.

Another object of the invention is to provide an expansile device and method of the above character in which tensioning means is provided for reversibly maintaining engagement of the expansile assembly against the vessel wall of a puncture by applying a substantially constant force of tension over a range of motion.

Another object of the invention is to provide an expansile device and method of the above character in conjunction with which a solid biological sealant is used by introduction into the puncture site or natural tract.

Another object of the invention is to provide an expansile device and method of the above character which permit placement of the device and biological sealant without requiring measurement, sizing, or dilation of the tissue tract.

Another object of the invention is to provide an expansile device and method of the above character wherein a sealant placement member is utilized for advancing said sealant into the body and placing the sealant external to the lumen of the vessel.

Another object of the invention is to provide an expansile device and method of the above character which provides a capsule or casing for compressing and delivering a solid sealant into the body and placing the sealant external to the lumen of the vessel.

Another object of the invention is to provide a biological sealant in the form of a gelatin slurry containing saline, thrombin and calcium.

Another object of the invention is to provide a biological sealant in the form of a Gelfoam® slurry containing saline, thrombin and calcium.

Another object of the invention is to provide a process for making a gelatin slurry biological sealant.

Another object of the invention is to provide a system and method for using a gelatin slurry biological sealant in conjunction with other vascular closure devices.

Additional objects and features of the invention will appear from the following description in which the preferred embodiments and the methods using the same are described in conjunction with the accompanying drawings.

FIG. 1 is a side-elevational view partially in section of a closure device for obtaining percutaneous access and occlusion of puncture sites in the human body incorporating the present invention and having closure means in a de-deployed or retracted position.

FIG. 2 is a cross-sectional view taken along the line 2—2 of FIG. 1.

FIG. 3 is a side-elevational isometric view of the distal end of the device shown in FIG. 1 with the closure means in a deployed or extended position.

FIG. 4 is a cross-sectional view taken along the line 4—4 of FIG. 3 and shows the manner in which a seal is formed with respect to a puncture.

FIGS. 5A–5D are cartoons demonstrating the method of using the device of the present invention for occluding a vascular access or puncture site.

FIG. 6 is a partial isometric view of an alternative closure assembly for the closure device shown in FIG. 1.

FIG. 7 is a side-elevational view partially in section of another embodiment of the closure device incorporating the present invention.

FIG. 8 is a cross-sectional view taken along the line 8—8 of FIG. 7.

FIG. 9 is a cross-sectional view taken along the line 9—9 of FIG. 8.

FIG. 10 is a side-elevational isometric view of the distal end of the device of FIG. 8 with the closure assembly in a deployed or expanded position.

FIG. 11 is a side-elevational view partially in section of another embodiment of the closure device incorporating the present invention.

FIG. 12 is a cross-sectional view taken along the line 12—12 of FIG. 11.

FIG. 13 is a partial side-elevational view of the distal extremity of the closure device of FIG. 11 with the closure mechanism in a deployed position.

FIG. 14 is a view looking along the line 14—14 of FIG. 13.

FIG. 15A is a side-elevational view partially in section of the proximal end of another embodiment of the closure device incorporating the present invention.

FIG. 15B is a side-elevational view partially in section of the distal end of the embodiment shown in FIG. 15A.

FIG. 16 is a side-elevational view partially in section of the distal end of the device of FIG. 15 with the closure assembly in a deployed position.

FIG. 17 is a view partially in section taken along the line 17—17 of FIG. 16.

FIG. 20 is an plan view of the top of the tensioning device of the present invention taken along the line 20—20 of FIG. 23.

FIG. 21 is a cross-sectional view taken along the line 21—21 of FIG. 23.

FIG. 22 is a side-elevational view partially in section of the tensioning device of the present invention in the open position.

FIG. 23 is side-elevational view partially in section of the tensioning device of the present invention in the closed, neutral position.

FIG. 27 is an isometric view of the device in FIG. 18 with another embodiment of the biological sealant introducing means.

FIG. 28 is an isometric view the third elongate member that obturates the second lumen in the biological sealant introducing means of FIG. 27.

FIG. 29 is a cross section view taken along the line 29—29 of FIG. 27.

FIG. 30 is a cross-sectional view of another embodiment of the third elongate tubular member which is part of the biological sealant introducing means of FIG. 27.

FIG. 31 is an isometric view of the device in FIG. 18 with another embodiment of the biological sealant introducing means.

FIG. 32 is a cross-section view taken along the line 32—32 of FIG. 30.

FIG. 33 is a side-elevational view partially in section of another embodiment of the closure or expansile device incorporating the present invention.

FIGS. 34A–C are cartoons demonstrating the method of using the device of FIG. 33 for occluding a vascular access or puncture site.

FIG. 35 is a side-elevational view partially in section of another embodiment of the closure or expansile device incorporating the present invention. FIGS. 36A–C are cartoons demonstrating the method of using the device of FIG. 36 for occluding a vascular access or puncture site.

Figure 37:
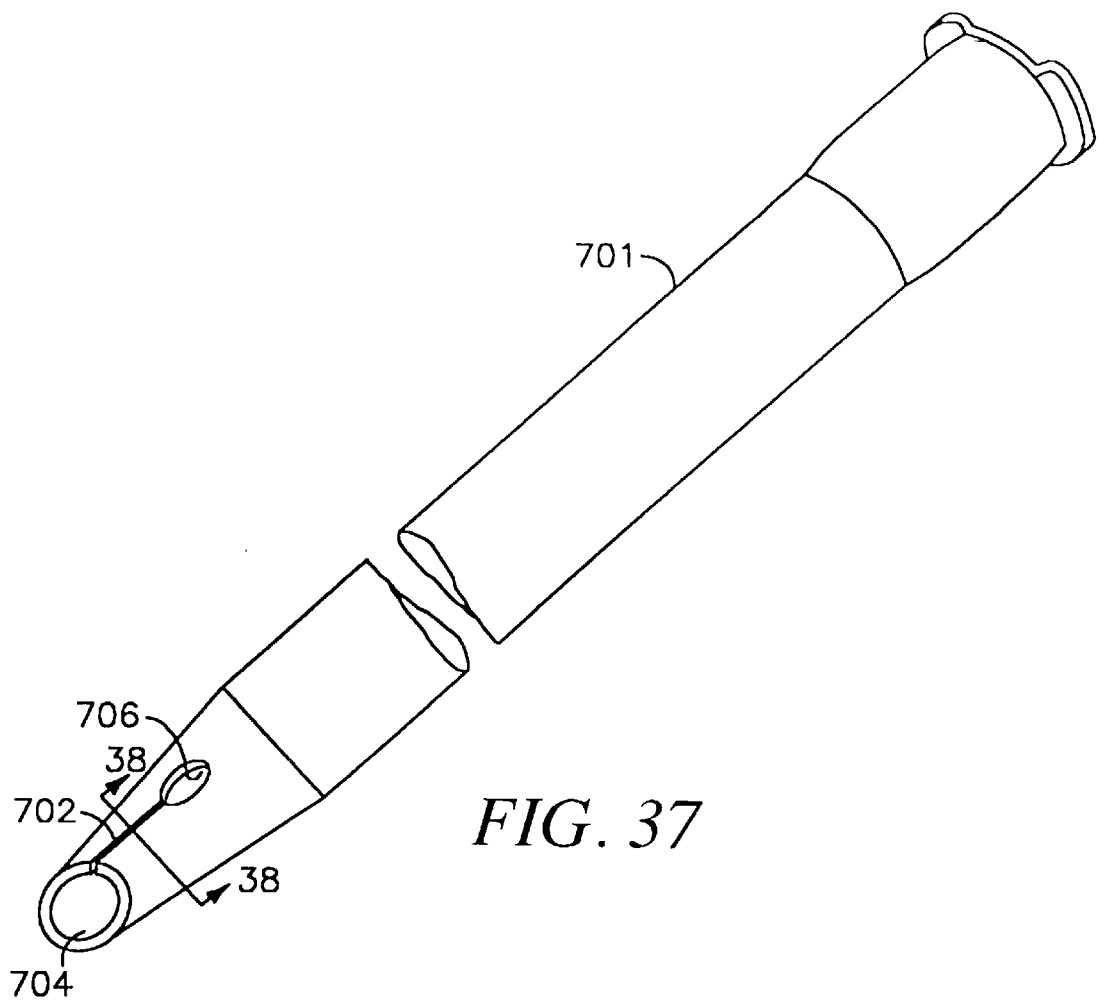

FIG. 37 is an isometric view of an injection sheath contained in the biological sealant system incorporating the present invention.

Figure 38:
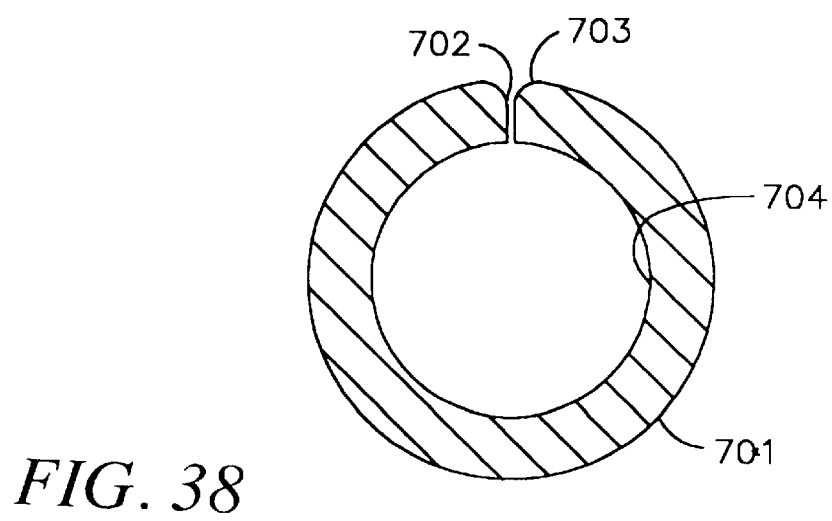

FIG. 38 is a cross section view taken along the line 38—38 of FIG. 37.

Figures 39A, 39B, 39C:
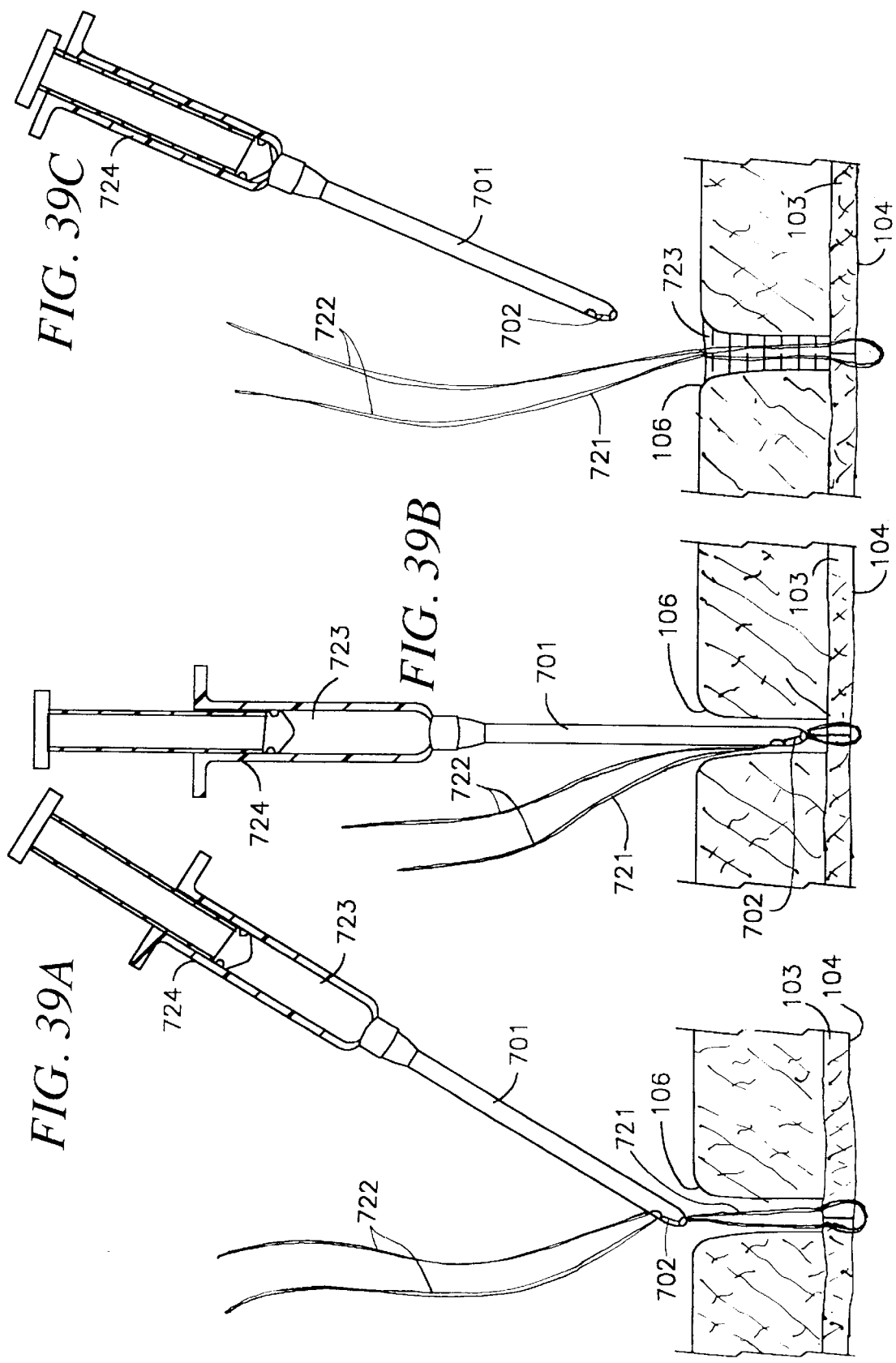

FIGS. 39A–C are cartoons demonstrating the biological sealant system and method of using a gelatin slurry biological sealant in conjunction with a vascular closure device utilizing sutures to occlude a puncture.

FIGS. 40A–C are cartoons demonstrating the biological sealant system and method of using a gelatin slurry biological sealant in conjunction with a vascular closure device utilizing an anchor, hemostatic plug and sutures to occlude a puncture.

FIGS. 41A–E are cartoons demonstrating the biological sealant system and method of using a gelatin slurry biological sealant in conjunction with a vascular closure device utilizing an insertion sheath and a mass of hemostatic material disposed therein.

In general, the closure device of the present invention is used for the percutaneous occlusion of a puncture site and natural tract in the human body. The human body has an outer layer of skin and inner layers of tissue surrounding a blood vessel having a lumen therein defined by a vessel wall. A puncture site traverses these layers and, in the case of a vascular access puncture, the vessel wall. The closure device comprises a flexible elongate tubular member having proximal and distal extremities, an outer diameter and extending along a longitudinal axis. The flexible elongate tubular member has a first lumen extending therethrough from the proximal extremity to the distal extremity. A closure assembly is carried by the distal extremity and includes a closure mechanism and an impermeable membrane at least partially covering the closure mechanism. Deployment means carried by the proximal extremity of the flexible elongate tubular member are adapted to be operated by the human hand. The deployment means extends through the flexible elongate tubular member, includes a push-pull wire and is coupled to the closure assembly for moving the closure assembly from a de-deployed or contracted position for introduction into and through a puncture to a deployed position for forming a seal occluding the puncture.

More specifically, as shown in FIGS. 1–4, the closure device 21 of the present invention for percutaneous occlusion of puncture sites and natural tracts consists of a flexible elongate tubular member 22 formed of a suitable plastic material such as polyethylene or polyurethane or polyimide. The flexible elongate tubular member 22 has a longitudinal axis and proximal and distal extremities 23 and 24. The flexible elongate tubular member 22 is provided with a main circular in cross-section first lumen 26 which may be centrally disposed extending from the proximal extremity 23 to the distal extremity 24. It is also provided with an additional or second lumen 27 which may be crescent-shaped as shown in cross-section in FIG. 2 extending from the proximal extremity 23 to the distal extremity 24 where it opens through an external port 28. A plug 29 of a suitable material such as plastic is placed in the lumen 27 to occlude the lumen 27 distal of the port 28.

The flexible elongate tubular member 22 is of a suitable size, as for example a diameter ranging from 1–9 French corresponding to an outside diameter ranging from approximately 0.3 to 3.0 millimeters. The flexible elongate tubular member has a suitable length as for example 15–30 centimeters with the external port 28 being disposed a suitable distance adjacent to and proximal of the closure assembly 32, as for example from 1–10 millimeters up to several centimeters. The first lumen 26 may have an inside diameter ranging from 0.015" to 0.080", preferably 0.020"–0.030" while the second lumen 27, if crescent-shaped may have a long axis dimension of approximately 0.015" to 0.080".

Closure means in the form of a closure assembly 32 is carried by the distal extremity 24 of the flexible elongate tubular member 22 and is coupled or secured to deployment means or mechanism 33 for movement from a contracted, retracted or de-deployed position to an expanded or deployed position. The closure assembly 32 includes a closure mechanism 34 and an impervious membrane 36 which covers the closure mechanism 34. The closure mechanism 34 as shown in FIGS. 3 and 4 is in the form of a complex geometrical configuration, as for example a coil, when in a free state. The coil 34 is formed of a suitable material which can be elongated without permanent deformation but when freed or unconstrained has a substantial portion thereof which will return to a generally planar or disk-like configuration to which it has been annealed. One material found to be particularly suitable for such an application is a super-elastic or shape memory element as formed of a nickel/titanium alloy, often called Nitinol. The coil 34 has a plurality of generally circular turns 37 and has first and second ends 38 and 39 secured to the deployment mechanism 33 in a manner hereinafter described. The turns 37 of the coil 34 lie in a single plane which is generally perpendicular to the longitudinal axis of the flexible elongate tubular member 22.

The coil 34 has a diameter which is selected to overlap a puncture site as hereinafter described to occlude the puncture site. Typically, a suitable diameter such as 3 to 7 millimeters and preferably approximately 5 millimeters is used. In the de-deployed configuration the constrained coil 34 has a suitable diameter ranging from 0.1 mm to 3.0 mm. The coil 34 can be formed of wire having a diameter ranging from 0.002" to 0.004" (0.05 to 0.1 millimeters) and preferably about 0.003" (0.076 millimeters). Alternatively, it can be formed of ribbon generally rectangular in cross-section and can have a thickness of approximately 0.001" to 0.002" (0.025 to 0.05 mm.) and a width of approximately 0.003" to 0.005" (0.076 to 0.13 millimeters).

The deployment means or mechanism 33 consists of a push-pull wire 41 which is slidably disposed in and extending through the first or main lumen 26 and has proximal and distal extremities 42 and 43. The push-pull wire 41 is formed of a suitable material such as stainless steel and has a suitable diameter as for example 0.005" to 0.032". Means is provided for securing the two ends 38 and 39 of the coil 34 to the distal extremity 43 of the push-pull wire 41 and consists of solder forming joints or adhesively bonded joints. As shown in FIG. 1 the proximal end 42 of the push-pull wire 41 extends out of the proximal extremity 23 of the flexible elongate tubular member 22 and is operatively connected to a handle assembly 44 as hereinafter described.

The handle assembly 44 is formed of a body 46 of suitable material such as plastic and is mounted on the proximal extremity 23 of the flexible elongate tubular member 22. The handle 44 is sized so it is adapted to be grasped by the human hand and is provided with means for operation of the push-pull wire 41 which includes a button 47 adapted to be engaged by a finger of the hand holding the handle. The button 47 is mounted on a protrusion 48 which is slidably mounted in a longitudinally extending slot 49 in the handle 44 and is movable between first and second positions for deploying the coil 34 from a retracted or contracted elongate position constrained within the flexible elongate tubular member 22 to an expanded position outside of the tubular member 22. The proximal extremity 42 of the push-pull wire 41 is secured to the protrusion 48 in a suitable manner such as a wire clamp or adhesive (not shown). The slot 49 opens into sideways extending notches 51 and 52 provided in the body which can receive the protrusion 48 in either the first or second position to retain the push-pull wire 41 in the desired position as hereinafter described.

The closure means 32 also includes a flexible impermeable membrane 36 which is carried by and secured to the distal extremity 24 of the flexible elongate tubular member 22. It is desired that this membrane 36 be very flexible and it therefore has a wall thickness ranging from 0.0005" to 0.010" (0.0127 to 0.076 millimeters) and preferably 0.001" (0.025 millimeters). It can be formed of any suitable flexible impermeable material such as elastomeric and non-elastomeric materials. For example, latex or silicone have been found to be suitable. The membrane 36 should be substantially impermeable to blood and other liquids. It is preferably formed as a tubular sock which can have an elongate generally cylindrical configuration with one closed end 54 and the other end circumscribed by an opening 56 which is defined by a rim 57 of the impermeable membrane. This rim 57 is circumferentially secured to the distal extremity 24 in a suitable manner such as by an adhesive (not shown) and preferably interiorly within the first or main lumen 26. However, if desired, the rim 57 can also be affixed exteriorly to the outer surface of the tip 31 of the distal extremity 24 of the flexible elongate tubular member 22. The impermeable membrane 36 is formed in such a manner so that it can, upon manufacture of the device 21, be disposed internally of the distal extremity 24 of the flexible elongate tubular member 22 and be folded inwardly with folds 58 in the main lumen 26 to accommodate closure mechanism 34 in a constrained, retracted or contracted or de-deployed position as shown in FIG. 1. It also has the flexibility of being moved outwardly by operation of the push-pull wire 41 to the sock-like dotted line position 61 shown in FIG. 1.

The impermeable membrane 36 also can be caused to assume a disk-like planar configuration as shown by the dotted-line position 62 in FIG. 1. This is accomplished by operation of the deployment mechanism 33 to move the push-pull wire 41 distally to urge the closure mechanism 34 distally to move out of the lumen 26 into the dotted-line position 61. As soon as the closure mechanism 34 is clear of the main lumen 26, it will expand into its memorized configuration. As this expansion is occurring, the membrane 36 covering the coil 34 is caused to move from the sock-like configuration 61 to the disk-like circular configuration 62 so that the membrane 36 is disposed on opposite sides of the closure mechanism 34 and lies in generally parallel planes which are generally perpendicular to the longitudinal axis of the flexible elongate tubular member 22 for percutaneously occluding a puncture as hereinafter described. The deployed closure mechanism 34 is sufficiently rigid so as to provide a supporting framework for the membrane 36.

The closure device 21 also consists of biological sealant introducer means 81 carried by the handle 44 and the flexible elongate tubular member 22 for introducing a biological sealant into a puncture proximal of the closure assembly 32 after the closure assembly 32 has been positioned. The biological sealant is of a suitable type such as a two-component fibrin glue, thrombin, fibrin, collagen-thrombin, collagen, Avitene (trademark), Gelfoam (trademark), cellulose, gelatin, and mixtures or slurries thereof.

One such mixture which assists hemostasis comprises a gelatin slurry. The slurry is made, preferably under sterile conditions and at room temperature, by the process of mixing gelatin powder with saline or water, preferably adding thrombin powder and calcium ions. A buffer may also be added to the solution. The mixture is blended to obtain a homogenous slurry which demonstrates superior flow characteristics in that it exhibits minimal dilatency in comparison to Avitene® and other collagen mixtures. This quality provides a hemostatic agent which can be easily injected or introduced through catheter lumens, especially small lumens.

More specifically, Gelfoam® powder is commercially available from Pharmacia & Upjohn. It is a heat-sterilized, water-insoluble, non-elastic, porous, pliable fine gelatin powder obtained from milling absorbable gelatin sponge which has been derived from purified porcine skin. The slurry of the present invention is obtained by blending Gelfoam powder with saline to obtain a 0.5–20 per cent solution by weight. Thrombin powder is added in the amount ranging from 1–20,000 units per milliliter of solution, preferably, 1,000 units per milliliter of solution. Preferably, calcium is added in the form of calcium gluconate, calcium chloride, calcium citrate or any other suitable calcium preparation in which case the slurry can be buffered. A calcium ion concentration ranging from approximately 1–500 milli-moles per milliliter of liquid is obtained. Preferably, a concentration of 8 milli-moles per milliliter is obtained by adding calcium chloride.

The ingredients for the gelatin slurry can be provided in a sterilely pre-packaged biological sealant system or kit. The system comprises a pre-determined quantity of Gelfoam powder packed in a first syringe which can be connected to a first female fitting of a three-way stopcock and a predetermined quantity of thrombin powder placed in a second syringe which can be connected to a second female fitting, preferably both Luer fittings, of the three-way stopcock. A sterile vial is also provided and includes a predetermined quantity of saline or water diluent with or without a predetermined quantity of calcium gluconate or calcium chloride. Accordingly, during a percutaneous vascular puncture closure procedure, when the operator is ready to inject the biological sealant, the system is opened under sterile conditions. The Gelfoam slurry is blended by, preferably, first adding the contents of the vial to the syringe containing the thrombin. Next, the two syringes are connected to the three-way stopcock and, by directing the three-way stopcock into a position wherein the two pre-loaded syringes are in communication with one another, the thrombin solution is injected into the syringe containing the Gelfoam. The mixture created thereby is then injected back into the empty syringe. The repeated, alternating deployment of the syringe plungers easily and effectively blends the contents of the two syringes to create a homogenous Gelfoam-thrombin slurry which can be deposited in one of the syringes. The kit or system can also include a modified injection catheter 701 for use in conjunction with other vascular closure devices. The catheter 701, shown in FIG. 37, is a conventional catheter made of a suitable material such as plastic and having a diameter ranging from 3–10 French and a length ranging from 2–10 inches. As shown in FIGS. 37–38, the distal end of the catheter 701 carries a longitudinal slit or slot 702 which extends proximally a variable distance from the distal-most tip of the catheter 701. As shown in Figure the slit 702 carries a bevel 703 directed towards a lumen 704 in the catheter 701. The proximal end of the slit 702 in the catheter 701 is provided with an enlarged portion, or eye 706. It should be appreciated that the entire length of the catheter 701 can be slit. As hereinafter described, this system facilitates introduction of the Gelfoam slurry when used with other vascular closure devices.

It should be appreciated that other biological sealants or pharmacological agents may also be introduced into a puncture utilizing this device.

The biological sealant introducer means 81 can consist of a fitting of a suitable type such as a wye adapter 82 which is provided with first and second arms 83 and 84 with first and second syringes 86 and 87 removably mounted thereon on and containing the two separate constituents of fibrin glue being used as the biological sealant. The fitting 82 is connected to a flexible tubular member 91 which is sealed into the handle 44 and is provided with a lumen 92 therein in communication with the lumen (not shown) of the arms 83 and 84. The distal end of the flow passage 92 in the tubular member 91 is aligned to be in communication with the second lumen 27 of the flexible elongate tubular member 22 so that when the syringes 86 and 87 are operated the biological sealant components are mixed and pass through the flow passage 92 existing via the external port 28 of the second lumen 27.

Operation and use of the device 21 in performing the method of the present invention in the percutaneous access and occlusion of vascular access sites and other puncture sites in the human body may now be described in conjunction with the cartoons shown in FIGS. 5A–5D. Let it be assumed that a percutaneous femoral arterial catheterization is to be performed. After sterile preparation, a thin-walled hollow needle with syringe (not shown) is percutaneously inserted through the skin 101, the underlying subcutaneous tissue 102 and then through the wall 103 defining the lumen 104 of a vessel 107 such as the femoral artery to form a puncture 106. Intra-arterial access is confirmed by the aspiration of arterial blood. A flexible wire (not shown) is then passed through the needle into the artery 107 and the needle is removed, leaving only the wire in place in the puncture 106. A vessel dilator (not shown) with a shorter conventional over-lying sheath 111 is passed over the wire through the puncture 106 into the lumen 104 after which the wire and dilator are removed. The sheath 111 extends from outside the patient through skin 101 and subcutaneous tissues 102 and through the wall 103 into the lumen 104 as shown in FIG. 5A. Various diagnostic and therapeutic catheters and other similar medical devices can be passed through the sheath 111, whose diameter can range from 3 to 24 French, to perform desired procedures, as for example an angioplasty procedure during which time anti-coagulants such as heparin have been introduced. At the conclusion of any such procedure, such instruments are removed leaving only the sheath 111 in place.

Let it be assumed that it is now desired to seal the puncture 106. The closure device 21 of the present invention with the closure assembly 32 in the retracted position as shown in FIG. 1 is inserted into the sheath 111 while maintaining standard sterile precautions. The distal extremity 24 of the flexible elongate tubular member 22 is passed through the sheath 111 and into the lumen 104 so that it extends a short distance up to several inches beyond the distal extremity of the sheath 111 as shown in FIG. 5A. The sheath 111 is then slowly, incrementally withdrawn proximally while maintaining the device 21 as stationary as possible. As can be seen from FIG. 5B, the flexible elongate tubular member 22 has a length so that the sheath can be removed from the puncture 106 while retaining the distal extremity 24 in the lumen 104 and without removing the handle 44. When the sheath 111 has been withdrawn as shown in FIG. 5B, the closure assembly 32 may be deployed by operation of the deployment mechanism 33. Alternatively, the distal extremity 24 of the flexible elongate tubular member 22 can be passed into the lumen 104 a slightly greater distance, the device 21 deployed with the sheath 111 still in position, and then both the sheath 111 and device 21 slowly withdrawn so that the sheath 111 is removed from the lumen 104 with the deployed device 21 appropriately positioned in the lumen 104.

Before deployment of the closure assembly 32, the finger button 47 is in its most proximal-most position with the protrusion 48 being seated in the notch 51 as shown in FIG. 5A. Now let it be assumed that it is desired to move the closure assembly 32 from a contracted or retracted position where it is disposed within the first main lumen 26. When it is desired to move the closure assembly 32 to an expanded or open position, the button 47 is retracted from the notch 51 and slidably advanced along the slot 49 to push the distal extremity 43 of the push-pull wire 41 distally to cause the Nitinol closure mechanism 34 to be advanced distally and to carry the folded impermeable membrane 36 out of the first or main lumen 26 to cause it to assume a sock-like shape as shown in position 61 in FIG. 1. Continued forward movement of the finger button 47 causes further longitudinal movement of the push-pull wire 41 which causes further distal movement of the closure mechanism 33 until it clears the first lumen 26 so that it is substantially free to cause it to expand into its super-elastic or shape memory form of a coil to carry with it the flexible impervious membrane 36 to assume the disk-like configuration represented by position 62 as shown in FIGS. 1 and 4. The finger knob is then positioned so that the protrusion 48 is seated in the notch 52.

After the closure mechanism has been fully deployed, the handle 44 can be utilized to gradually retract the flexible elongate member 22 to ensure that the proximal surface of the flattened flexible membrane 36 is brought into close engagement with the inner surface of the wall 103 forming the lumen 104 in which the closure assembly 32 is disposed. This forms a liquid tight seal between the closure assembly 32 and the wall 103 immediately adjacent the puncture 106 which in turn enables accurate and effective deposition of the biological sealant into the puncture 106 as hereinafter described. Such a liquid tight seal is also necessary in connection with the present invention to prevent the leakage of blood through the puncture 106. This serves to prevent blood from interfering with attempts to safely and permanently occlude and seal the puncture 106 and to prevent inadvertent intravascular deposition of sealant.

The formation of a good seal between the occlusion assembly 32 and the wall 103 of the vessel 107 can be ascertained in several ways. By way of example the absence of arterial blood in the puncture 106 serves to verify that a good seal has been made. Attempts to aspirate blood from the second lumen 27 with no blood return therefrom also indicates accurate placement of the device 21. Alternatively, fluoroscopy can be utilized to check the position of the closure assembly 32. This is made possible because of the radio opacity of the closure mechanism 34. Radio opaque dyes may also be utilized to ascertain whether the puncture has been effectively sealed. A small amount of radio opaque dye may be injected into the subcutaneous tissue adjacent the puncture 106. If fluoroscopy demonstrates intravascular dye then there is inadequate placement of the closure assembly 32. If perchance there is any leakage, the button 47 can be engaged by the finger and retracted out of the notch 52 and proximally for a slight distance and then moved distally to re-deploy the mechanical assembly 32, thereafter grasping the handle 44 and pulling the flexible elongate member 22 proximally to again reestablish a seal with the wall 103 adjacent the puncture 106.

As soon as it has been established that a good seal has been formed in the manner hereinbefore described between the closure assembly 32 and the wall 103 adjacent the puncture 106, a biological sealant to be utilized can be introduced into the puncture 106 to provide a sealant 116 which extends throughout the puncture 106 from immediately outside the vessel 107 up to as far as the outer surface of the skin 101 as shown in FIG. 5C. It should be appreciated, however, that it may not be necessary to introduce an amount of sealant so great as to cause it to extend proximally to the skin. Assuming that the biological sealant is a fibrin glue supplied in two ports in the syringes 86 and 87, the physician utilizing the closure device 21 while holding the handle 44 in one hand utilizes the other hand to operate the syringes 86 and 87 to cause the constituents of the biological sealant to be introduced into the wye adapter 82 where they are mixed with each other and introduced through the tubular member 91 and into the second lumen 27, thence through the exit port 28 which is adjacent the closure assembly 32. It should be appreciated that in addition to holding the handle 44 in order to maintain engagement of the closure assembly 32 with the vessel wall 103, any suitable device by way of example a pin-vise may be applied to the flexible elongate tubular member 22 immediately adjacent the skin 101 so that the engagement is maintained and the physician has a free hand. The fibrin glue seals the innermost tissue layers in the puncture 106 and then, as hereinbefore described, can backfill the puncture 106 through the subcutaneous tissue 102 and to the skin 101, surrounding the distal extremity 24 of the flexible elongate tubular member 21 as shown in FIG. 5C. If necessary, the completion of this backfilling can be observed by the fibrin glue exiting from the puncture 106. As soon as this occurs, the physician terminates further movement of the syringes 86 and 87 and then while still holding the handle 44 to retain the closure assembly 32 in place, permits the fibrin glue to set up or cure within the puncture 106 for a period of time suitable to permit the fibrin glue to form a sticky adherent clot in the puncture 106 but to prevent the fibrin glue forming a clot which is too firm so as to preclude easy withdrawal of the closure device 21. Typically this ranges from a period of time of 30 seconds to 15 minutes and preferably a period of time of approximately 1–2 minutes.

The aforementioned biological sealants only adhere to collagen-containing tissues which prevents them from bonding to the flexible elongate tubular member 22. As soon as the physician determines that the fibrin glue has assumed the desired state, the button 47 carried by the handle 44 is engaged by the finger of the physician's hand and moved out of the slot 52 and then retracted proximally in the slot 49 to cause proximal movement of the push-pull wire 41 to cause a gradual straightening of the closure mechanism 34 to bring it substantially within the interior of the lumen 26 thereby permitting collapse of the flexible membrane 36 so that it can assume a generally sock-like configuration. Thus as soon as the button 47 has been moved to its most proximal position and moved into the notch 51, the closure device 21 can gently be pulled from the seal 116 provided in the puncture 107. The hole (not shown) left in the sealant 116 after withdrawal of the flexible elongate tubular member 22 and the membrane 36 carried thereby closes on itself due to the sufficiently gel-like state of the fibrin glue or other agent. Thereafter, the site of the puncture 106 is observed to ascertain whether or not bleeding is occurring therefrom. An excellent biological seal is formed with nothing remaining at the puncture site except for the biological sealant which within a relatively short period of time as for example 1–2 weeks will be absorbed by the body.

From the foregoing it can be seen that there has been provided a closure device and a method for utilizing the same which makes it possible to quickly and efficaciously close the puncture which has been made necessary for performing a desired medical procedure as for example an angioplasty procedure. An excellent seal is formed even though anticoagulants have been introduced into the blood of the patient during the procedure to prevent the formation of clot. The application of fibrin glue in this manner permits the formation of a good clot to seal the puncture without danger of re-bleeding occurring.

It also should be appreciated that during this procedure in performing the closure of the puncture site, blood can continue to flow substantially unimpeded through the lumen 104 of the vessel. This lack of obstruction is made possible because of the small size of the distal extremity of the closure device 21 and also because of the small size of the closure assembly 32 carried by the distal extremity 24 of the device 21. When the closure assembly 32 is deployed as hereinbefore described, it has a relatively small diameter in comparison to the size of the lumen into which it is introduced. In addition it has a flat planar configuration which, when brought into engagement with the inner surface of the wall 103, is substantially flush with the inner surface of the wall 103. Even when the closure assembly 32 is being de-deployed it occupies very little space as it is being withdrawn.

Another embodiment of the closure assembly is shown in FIG. 6 which can be utilized in place of the closure assembly 32 on the distal extremity 24 of the flexible elongate tubular member 22 carried by the handle 44. As shown, the closure assembly 131 consists of a closure mechanism 132 which is covered by a flexible impermeable membrane 133. The closure mechanism 132 can be formed of the same super-elastic or shape memory material as the closure mechanism 34 but rather than having a coil-like configuration such as shown in FIG. 1, 3 and 4, it includes a different complex geometrical configuration as for example a flower-like configuration as shown in FIG. 6. Thus it can be formed of a Nitinol ribbon or wire of a single length having ends 137 and 138 which are secured to the distal extremity 43 of the push-pull wire 41 in a manner similar to that hereinbefore described. The wire ribbon 136 has been annealed to have a super-elastic or shape memory form for the flower-like configuration shown in which a plurality of loops 141, as for example three as shown are provided on the wire ribbon 136. The loops 141 are oval shaped, approximately equal in size and have curved outer extremities 142. The loops 141 lie in a single plane and have the longitudinal axes of the loops spaced apart by equal angles of about 120°. It should be appreciated that if desired, additional loops can be provided with the loops being spaced equally over 360°. Since the loops 141 correspond to the shape of petals of a flower, the configuration shown in FIG. 6 can be described as a flower-like arrangement in which the loops 141 lie in a common plane which is generally perpendicular to the longitudinal axis of the flexible elongate member 22.

The membrane 133 which forms a part of the closure assembly 131 can be formed of the same material as the membrane 36 and can be secured in the same manner to the tubular member 22 so that when the closure mechanism 132 is in a retracted position within the lumen 26 it also can be provided with folds in the same manner as the membrane 36. The closure mechanism 132 can be straightened in a similar manner and brought into a retracted position similar to the closure mechanism 34. The closure assembly 131 also can be deployed in a similar manner. When deployed, it will cause the impermeable membrane to assume a generally flat planar configuration which is still substantially in the form of a circle as determined by the outer curved extremities 142 of the loops 141 with very slight variations from a circle between the outer extremities of adjacent loops. Thus a good seal can be formed with the wall 103 of the vessel 107 in the same manner as with the closure assembly 32. Thus it can be seen that the operation and use of the closure assembly of FIG. 6 can be very similar to that described for use of the closure assembly 32 and with generally the same attendant advantages. It should be appreciated that other arrangements of closure mechanisms can be provided for causing appropriate deployment of the impervious membrane to form a seal without departing from the scope of the present invention. The sizes and shapes of the closure assemblies can be selected to be appropriate for the puncture to be occluded. Thus for example the flower arrangement shown in FIG. 6 can have the same size as the coil arrangement shown in FIGS. 1, 3 and 4 or alternatively can be decreased or increased in size as desired. Furthermore, by altering the number of petals or loops, the shape can also be varied from that of a circle to that of substantially a triangle or square.

Another embodiment of a closure device incorporating the present invention is shown in FIGS. 7–10. The closure device 151 is shown therein. The closure device is very similar to that shown in FIG. 1 with the principal difference being in the type of closure assembly utilized on the distal extremity 24 of the flexible elongate tubular member 22. Thus all of the parts of the closure device 151 carry the same numbers as the closure device 21 shown in FIG. 1 to the distal extremity 24 on which the closure assembly 156 is carried. The closure assembly 156 consists of a closure mechanism 157 which is covered by a flexible impermeable membrane 158. The closure mechanism 157 consists of a plurality of rod-like elements 161, struts or arms of at least three in number which are circumferentially spaced apart and have proximal ends 162 which are embedded in the distal extremity 24 of the flexible elongate tubular member 22. This can be accomplished in a suitable manner such as by extruding the plastic forming the tubular member over the proximal ends 162 or alternatively by placing axially aligned bores in the distal extremity 24 and securing the proximal ends 162 therein by suitable means such as an adhesive. The exposed portions of the rod-like elements 161 as shown in FIG. 7 are formed of a suitable material such as stainless steel or Nitinol and are inclined inwardly in a distal direction to provide a truncated cone-like shape. The distal ends 163 of the rod-like elements 161 can be bonded or fastened together in a suitable manner such as by welding or solder to provide a generally hemispherical tip 166 which is also secured to the distal extremity 43 of the push-pull wire 41. The rod-like elements 161 are provided with weakened regions or notches or memorized bending points 171 approximately a substantially equal distance from the proximal and distal ends 162 and 163 to form hinge points 171. The lengths of the exposed portions of the rod-like elements 161 may be selected to correspond to a selected diameter of the closure mechanism 157.

The membrane 158 which covers the closure mechanism 157 has a sock-like configuration with a closed end 176 which overlies the hemispherical tip 166 and an a open end which is defined by the circular rim 177 which is bonded to the exterior surface of the distal extremity 24 of the flexible elongate tubular member 22 by an adhesive (not shown).

Operation and use of the closure device 151 may now be briefly described as follows. It should be appreciated that imposition of the button 47 with respect to the notches 51 and 52 is reversed in that the button is positioned in the notch 52 when the closure assembly 156 is in the de-deployed or unexpanded condition as shown in FIG. 7 rather than in the notch 51. A closure device 151 can be introduced into the sheath 111 in the unexpanded condition shown in FIG. 7 in the manner hereinbefore described with respect to the device 21 and after the closure assembly 156 is within the lumen 104 of the vessel 107 the closure assembly 156 can be deployed or moved to an expanded position by moving the button 47 proximally to cause a pulling force to be applied to the hemispherical tip 166 to cause a pushing force to be applied to the rod-like elements 161 to cause them to be bowed outwardly and to bend or fold about the hinge points 171 and at the same time to carry with them the membrane 158. Continued movement of the button 47 proximally until it reaches the slot 51 will cause the rod-like elements 161 to cause the portions 161a to generally overlie the portions 161b and to extend radially from the longitudinal axis of the flexible elongate tubular member 22 at substantially right angles thereto as shown in FIG. 10. The membrane 158 covering the same is similarly caused to assume a generally circular disk-like configuration lying in a single plane which can be brought against the inner surface of the wall 103 of the vessel 107 in the same manner that the closure assembly 32 hereinbefore described is brought into contact with the wall. Thereafter the procedure hereinbefore described can be used for forming the seal with the puncture 106 and to permit introduction of the biological sealant. After this procedure has been completed, the closure mechanism 157 can be de-deployed by moving the same to an unexpanded condition by moving the knob 47 proximally to cause the push-pull wire 41 to move the hemispherical tip 166 distally and to carry with it the membrane 158 until the closure assembly 156 assumes its original unexpanded or de-deployed generally cylindrical configuration which is in alignment with the longitudinal axis of the flexible elongate tubular member 22 as shown in FIG. 7 after which the closure device 151 can be removed to form the desired occlusion for the puncture 106. It should be appreciated that by varying the number of rod-like elements the shape of this closure assembly can similarly be varied so that it may be deployed into planar triangular, square or oval configurations as well. This closure assembly 156 also differs from the closure assembly 32 and the closure assembly 131 in that it can be formed without the use of super-elastic or shape memory material.

Another embodiment of a closure device incorporating the present invention is shown in FIGS. 11, 12 and 13 in which a closure device 191 is shown which is very similar to the closure device shown in FIG. 7 with the exception that the closure assembly carried by the distal extremity 24 of the flexible elongate tubular member 22 is of a different construction from the closure assembly 156. The closure assembly 196 differs from the closure assembly 156 in that the distal extremity 24 of the flexible elongate tubular member 22 carries an additional segment 192 of flexible elongate tubular material which has been bonded or annealed to the tip 31 of the distal extremity 24 of the flexible elongate tubular member 22 and which forms a part of a closure mechanism 197 which is covered by an impermeable flexible membrane 198. The additional segment 192 is constructed of a segment of flexible elongate tubular member which is extruded with only a main circular in cross-section first lumen and without an additional lumen. The second lumen 27 in this device 191 is blocked by the bonded or annealed additional segment 192 and thus no plug is required. To form the closure mechanism 197, the additional segment 192 of the flexible elongate tubular member 22 is provided with a plurality of circumferentially spaced apart longitudinally extending slits 201 of a suitable number to provide a plurality of arcuate segments as for example the four segments 24a, 24b, 24c and 24d as shown in FIGS. 11 and 12. As hereinafter described since the segments 24a, b, c and d are formed of a flexible material, they can be bowed outwardly. The closure assembly 196 also includes a plurality of rod-like elements 202 similar to the rod-like elements 161 and formed of a suitable material such as stainless steel or Nitinol but because of the use of the arcuate segments 24a, b, c and d the rod-like elements 202 need only be approximately one-half the length of the rod-like elements 161. The rod-like elements 202 like the rod-like elements 161 can have a suitable diameter as for example 0.002" to 0.015" or preferably 0.002" to 0.003". The rod-like elements 202 are provided with proximal and distal ends 203 and 204. The proximal ends are embedded in the arcuate segments 24a, b, c and d in a suitable manner. For example, the plastic forming the segments can be extruded over the ends 203 or, alternatively, the segments can be provided with bores for receiving the ends 203 which are secured therein by suitable means such as an adhesive (not shown). The rod-like elements 202 extend distally and inwardly to form a truncated cone and have their distal ends 204 interconnected by a generally hemispherical tip 206 formed of solder or a weld which is also bonded to the distal extremity 43 of the push-pull wire 41 as shown in FIG. 11. The rod-like elements 202 are provided with notches or weakened regions or memorized bending points to form hinge points 208 which are preferably in close proximity to the arcuate segments 24a, b, c and d so that the hinge points are close to the junctures between the ends 203 and the adjoining segments 24a, b, c and d. The length of each of the arcuate segments 24a, b, c and d and each of the rod-like elements 202 is approximately equal and corresponds to the desired size of the closure mechanism 197.

The membrane 198 covers the closure mechanism 197 and has a conformation similar to that of the membrane 158 and is provided with a closed end 211 which overlies the hemispherical tip 206 and an open end circumscribed by a rim 212 which is adhered to the additional portion 192 of flexible elongate tubular material annealed to the tip 31 of the distal extremity 24 of the flexible elongate tubular member 22 just proximal of the slits 201 which form the segments 24a, 24b, 24c and 24d and is secured thereto by a suitable means such as an adhesive (not shown).

Operation and use of the closure device 191 as shown in FIGS. 11 and 12 is very similar to that described for the embodiment of the closure device 151 shown in FIG. 7. The closure device as shown in FIG. 11 has the closure assembly 196 in a de-deployed or un-expanded condition with the button 47 being disposed in the notch 52. In connection with sealing a puncture after the distal extremity 24 of the device 191, and in particular the closure mechanism 197, is disposed within the vessel 107 distal of the puncture 106, the closure assembly 196 can be deployed by moving the button 47 proximally to cause pulling on the pull wire 41 to apply compressive forces to the strut-like rod-like elements 202 to cause outward bowing of the same as well as the segments 24a, 24b, 24c and 24d with sharp bends occurring at the hinge points 208 just distal of the arcuate segments 24a, b, c and d. This outward bowing is continued so that the arcuate segments 24a, b, c and d are bent outwardly with respect to the longitudinal axis of the flexible elongate tubular member 22 and similarly the rod-like strut elements 202 are bowed outwardly with respect to the hemispherical tip 206 while carrying along with them the flexible impermeable membrane 198 until the rod-like elements 202 substantially overlie and are generally parallel with the segments 24a, b, c and d as shown in FIGS. 13 and 14 to form a planar disk-like conformation corresponding generally to the disk-like conformations of the embodiments of the closure devices hereinbefore described. Although the conformation as viewed in FIG. 14 has a generally square configuration it can be readily appreciated that by providing additional segments in the distal extremity 24 and a corresponding number of additional rod-like elements, additional arms can be provided for controlling the movement of the membrane 198 so that the outer margin of the membrane has a more generally circular configuration if that be desired. As heretofore described with other embodiments, the configuration may also be oval, triangular or square depending on the number of elements.

After the closure assembly 196 has been deployed as shown in FIGS. 13 and 14 it can be utilized in the manner hereinbefore described with the previous closure devices for forming a seal with the inner surface of the wall 103 and thereafter introducing a biological sealant. After this has been accomplished, the closure assembly 196 can be contracted and de-deployed by moving the button 47 from the notch 51 and pushing it distally to push the hemispherical tip 206 distally and to cause inward collapsing of the segments 24a, b, c and d and the rod-like strut elements 202 until they have been moved into the original de-deployed or contracted positions as shown in FIG. 11 and with the button 47 in the notch 52. Thereafter, the closure device 191 can be retracted in a manner similar to that hereinbefore described with respect to the previous embodiments.

Another embodiment of a closure device incorporating the present invention is shown in FIGS. 15 and 16. The closure device 221 shown therein is similar to that shown in FIG. 1 with the principal differences being that the device 221 utilizes a closure assembly on the distal extremity 24 of the flexible elongate tubular member 22 and a deployment means that incorporate elements that are similar to both the device shown in FIG. 1 and the device shown in FIGS. 7–10. The closure assembly 222 consists of a closure mechanism 223 and an impervious membrane 224 which covers the closure mechanism 223. The closure mechanism 223 can be formed of the same super-elastic or shape memory material as the closure mechanism 34 but rather than having a coil-like configuration it consists of a plurality of circumferentially spaced apart rod-like elements 226 or arms of at least three in number having proximal and distal ends 227 and 228. Thus each rod-like element 226 can be similarly formed of Nitinol ribbon or wire and is annealed with an approximate 180 degree fold located at the midpoint 229 between the proximal 227 and distal 228 ends so that when in a free state the element 226 tends to fold at the midpoint 229 causing the proximal and distal halves 231 and 232 of the rod-like element 226 to substantially overlie one another in a single plane. Means is provided to secure the proximal end 227 of each rod-like element 226 to the deployment mechanism 230 in a manner hereinafter described. The distal ends 228 of the rod-like elements 226 are fastened together in a suitable manner such as by welding or soldering to provide a generally hemispherical tip 233 which is also secured to the deployment mechanism 230 in a manner hereinafter described. Similar to the closure device 151 shown in FIGS. 7–10, the lengths and number of the rod-like elements 226 may be selected to correspond to a selected diameter and shape of the closure mechanism 223.

The membrane 224 which forms a part of the closure assembly 222 can be formed of the same material as the membrane 36 and can be secured in the same manner to the tubular member 22 so that it is provided with folds and functions in the same manner as the membrane 36.

The deployment mechanism 230 consists of a push-pull wire 234 formed of a suitable material such as stainless steel which is slidably disposed in the first or main lumen 26 and has proximal and distal extremities 236 and 237 similar to the push-pull wire 41 with the principal difference being that during formation the push-pull wire 234 is provided with a central lumen or bore 238 extending from the proximal extremity 236 to the distal extremity 237. The push-pull wire 234 has a suitable outside diameter of approximately 0.020" (0.5 millimeters) and an inside diameter of approximately 0.010" (0.25 millimeters). Means is provided for circumferentially securing the proximal ends 227 of the rod-like elements 226 to the distal extremity 237 of the push-pull wire 234 with the secured proximal ends 227 of the elements 226 being equally spaced apart over 360 degrees and with the vertex of each midpoint 229 fold directed outwardly and consists of similar welds or solder forming joints 239 and 241. The proximal end 236 of the push-pull wire 234 extends out of the proximal extremity 23 of the flexible elongate tubular member 22 and is connected to a handle assembly 242 in a manner similar to the device 21. The deployment mechanism 230 includes a second, smaller pull wire 243 which is slidably mounted or disposed within the central lumen 238 of the larger push-pull wire 234 and is provided with proximal and distal extremities 244 and 246. The pull wire 243 is similarly formed of a suitable material such as stainless steel and has a suitable diameter as for example 0.005" to 0.030". Means is provided for securing the distal extremity 246 of the pull wire 243 to the hemispheric tip 233 and consists of soldering or welding. The proximal end 244 of the smaller pull wire 243 also extends out of the proximal extremity 23 of the flexible elongate tubular member 22 and is operatively connected to the handle assembly 242 which, in addition to carrying means for causing longitudinal movement of the push-pull wire 234 hereinbefore described and shown in FIG. 1, also carries means for causing movement of the pull wire 243 along the longitudinal axis independent of the movement of the push-pull wire 234 in a manner hereinafter described.

The handle assembly 242 is similar to the handle assembly 44 with the principal difference being that the handle assembly 242 also provides access to the proximal end 244 of the smaller pull wire 243. The protrusion 247 of handle assembly 242 and means of securing the push-pull wire 234 to the same is similar to protrusion 48 but the protrusion 247 is also provided with a lumen 248 extending from the proximal end 249 to the distal end 251 of the protrusion 247 and aligned with the central lumen 238 of the proximal extremity 236 of the push-pull wire 234. A handle lumen 250 is provided which extends proximally from the proximal end of the handle slot 255 and is alignment with both the slot 255 and the proximal end 249 of the lumen 248 in the protrusion 247. The handle lumen 250 is provided with an aperture 252 at the proximal end of the handle 242. The proximal end 244 of the smaller pull wire 243 extends proximally out of the proximal end 236 of the push-pull wire 234 into and through the lumen 248 of the protrusion 247 and through the handle lumen 250 slidably extending proximally out of the handle assembly 242 through the aperture 252. Means for fixing the proximal end 244 of the pull wire 243 in a particular position is provided as for example with a simple releasable clamp or knob 253 that prevents the pull wire 243 from sliding distally.

Operation and use of the closure device 221 may now be briefly described as follows. It should be appreciated that operative positions of the button 254 for operation and use of the closure device 221 are similar to positions for button 47 in the closure device 21 shown in FIG. 1. A closure device 221 can be introduced into the sheath 111 in the un-expanded cylindrical or de-deployed configuration shown in FIG. 15 in the manner hereinbefore described with respect to the device 21. The closure assembly 222 also can be deployed and de-deployed in a similar manner with the principal difference being the additional steps of deploying and de-deploying the pull wire 243 in a manner hereinafter described. After the button 254 is similarly utilized to initiate and maintain deployment of the closure assembly 222 by pushing the closure mechanism 223 out of the distal extremity 24 of the flexible elongate tubular member 22, the rod-like elements 226 and the membrane 224 assume a configuration which is substantially in the form of a disk or a flattened circle, the shape being partially determined by the number of the rod-like elements 226. In order to assure assumption of a substantially flat planar configuration by the closure assembly 222 the small pull wire 243 is then pulled proximally and fixed in position by using the clamp 253, while the push-pull wire 234 is held stationary, to cause a pulling force to be applied to the hemispherical tip 233 to cause a pushing force to be applied to the rod-like elements 226 to cause them to further fold about their midpoints 229 so that the proximal and distal halves 231 and 232 of the elements 226 substantially overlie one another in a single plane at a substantially right angle to the longitudinal axis of the flexible elongate tubular member 22. Thereafter the procedure hereinbefore described can be used for establishing a seal of the puncture 106 and to permit introduction of the biological sealant. After this procedure has been completed, the closure assembly 222 can be de-deployed by releasing the clamp 253, permitting the small pull wire 243 to be pushed distally and then similarly completing the de-deployment sequence as hereinbefore described for closure device 21.

It should be appreciated that additional variations of the pull wire assembly may be utilized as for example means may be provided for mounting the pull wire within the lumen of the push-pull wire so that the position of the pull wire is fixed in relation to the longitudinal axis of the flexible elongate tubular member so that with independent longitudinal movement of the push-pull wire a similar pulling force is simultaneously applied to the hemispherical tip to cause a pushing force to be applied to the rod-like elements as hereinbefore described.

It should also be appreciated that other embodiments may incorporate closure assemblies utilizing arcuate segments similar to those shown in FIGS. 11, 12 and 13, absent rod-like elements wherein the distal tip of the push-pull wire is bonded directly to the tip of the distal extremity of the flexible elongate tubular member so that with proximal traction on the push-pull wire compressive forces applied to the arcuate segments cause outward bowing of the same with bends or folds occurring at the midpoints of the segments. An additional closure assembly may include a closure mechanism constructed of super-elastic or shape memory alloy that is deployed by pushing the closure mechanism distally out of the distal extremity of the flexible tubular member and then causing the super-elastic or shape memory alloy mechanism to be twisted by turning the proximal end of the push-pull wire. In various embodiments the impermeable membrane may also be secured directly to the closure mechanism instead of being secured to the distal extremity of the flexible elongate tubular member. Alternatively the membrane may be configured so to only partially cover the closure mechanism as for example only the proximal side of the deployed closure mechanism.

Figure 18:
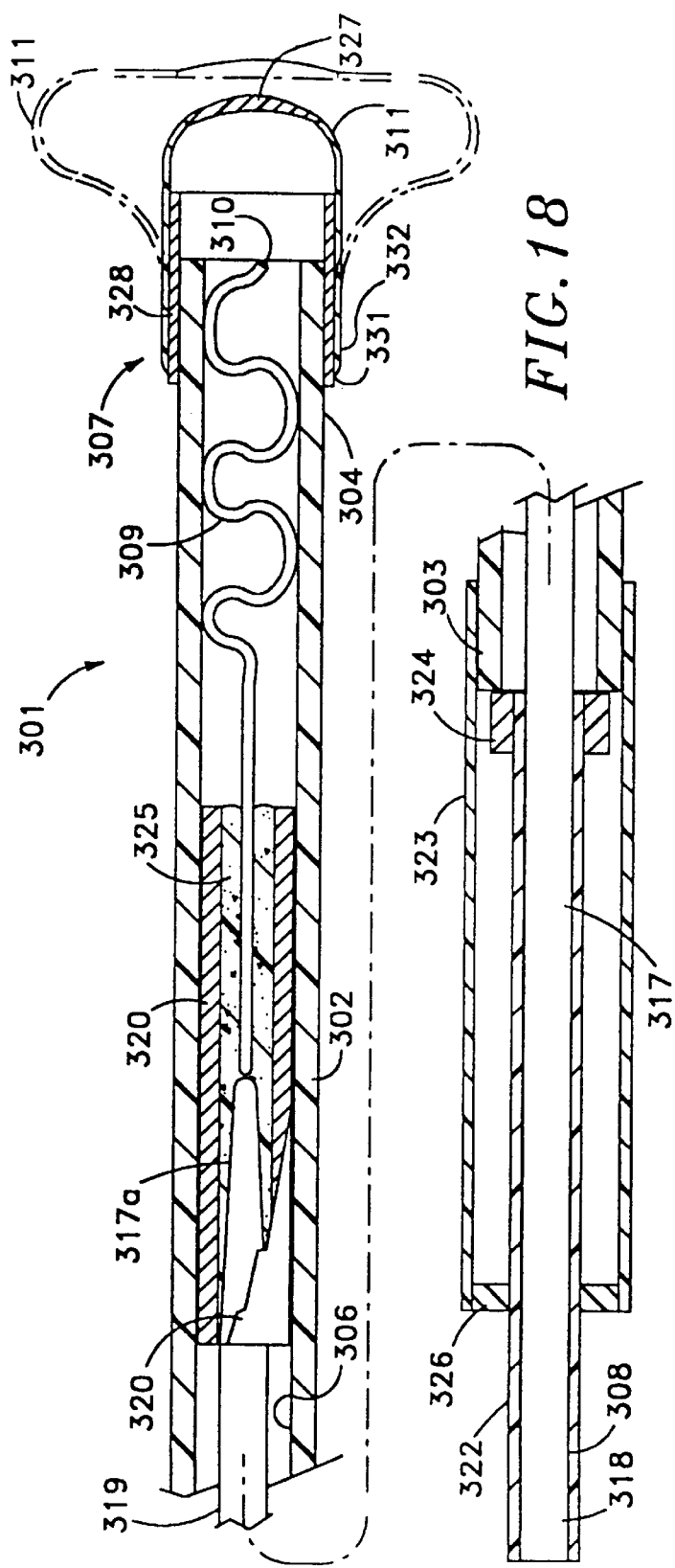
FIG. 18 is a side-elevational view partially in section of another embodiment of the closure or expansile device incorporating the present invention.
Figure 19:
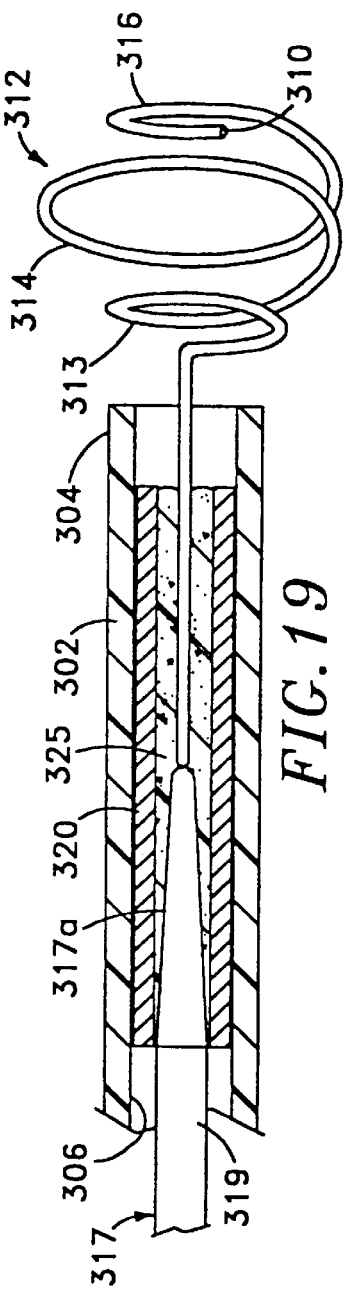
FIG. 19 is a side-elevational view partially in section of the distal end of the device of FIG. 18 with the expansile assembly in an free or expanded position without the covering membrane.

Another embodiment of an expansile or closure device incorporating the present invention is shown in FIGS. 18–19. The device 301 shown therein consists of a first elongate tubular member 302, preferably a flexible elongate tubular member 302, formed of a suitable plastic material, preferably a cast thermoset material such as polyimide. The first flexible elongate tubular member 302 has proximal and distal extremities 303 and 304 with a longitudinal axis extending from the proximal 303 to the distal extremity 304 and is provided with a first lumen 306 circular in cross-section which, as shown, may be centrally disposed extending from the proximal extremity 303 to the distal extremity 304. Both the outer and inner surfaces of the polyimide member 302 may be coated with a lubricious material such as Teflon™. Alternatively, the thermoset material may be a polyimide-Teflon™ or polyimide-Nylon-Teflon™ composite in order to provide the desired lubricious inner and outer surfaces. The first flexible elongate tubular member 302 has an outside diameter ranging from approximately 0.008" to 0.050", preferably approximately 0.018". The first flexible elongate tubular member 302 has a suitable length as for example 10–150 centimeters. The first lumen 306 in the first flexible elongate tubular member 302 may have an inside diameter of approximately 0.0031" to 0.030", preferably 0.012".

Expansile means in the form of an expansile assembly 307 is carried by the distal extremity 304 of the first flexible elongate tubular member 302 and is movable between contracted and expanded positions. A deployment mechanism 308 is carried by the proximal extremity 303 of the first flexible elongate tubular member 302 and adapted to be operated by the human hand for movement from a contracted position to an expanded or deployed position.

The assembly 307 includes a expansile member 309 and a membrane 311 which covers the expansile member 309. The expansile member 309 as shown in FIG. 19 is in a form having a complex geometrical configuration, preferably a helical coil configuration 312, when in a free state. The helical coil 312 is formed of a suitable material, preferably Nitinol, which can be elongated or constrained without permanent deformation but, at body temperature, when freed or unconstrained returns to the helical coil configuration to which it has been annealed. The helical coil 312 has a plurality of generally circular turns creating, preferably, a proximal turn 313, a middle turn 314 and a distal turn 316. The proximal, middle and distal turns 313, 314, 316 are generally nonplanar with respect to one another. The proximal and distal turns 313 and 316 each lie in a plane that is generally parallel to one another and generally perpendicular to the longitudinal axis of the first flexible elongate tubular member 302. The middle turn 314 is non-planar and helical as it connects the proximal and distal turns 313 and 316 so that the unconstrained helical coil configuration assumes a bi-conical shape.

The middle turn 313, when freed or unconstrained, has a suitable diameter ranging from 2 to 10 millimeters and preferably 4 to 6 millimeters is used. As hereinafter described, during deployment the middle turn 313 is partially flattened and constrained by the membrane 311 to assume a diameter ranging from 1 to 10 millimeters, preferably 11 French, in order to overlap a puncture site to assist in occluding the puncture site. The proximal and distal turns 313 and 316 are of approximately equal size and diameter ranging from 1 to 5 millimeters, preferably 2 to 3 millimeters. The unconstrained helical coil 312 configuration has a distance from the proximal 313 to the distal turns 316 of approximately 3 to 15 millimeters, preferably 5 to 8 millimeters. In the de-deployed configuration the helical coil 312 is retracted into the first flexible elongate tubular member 302 and has a contracted, constrained diameter corresponding to the approximate diameter of the Nitinol wire used to construct the expansile mechanism 309, ranging from 0.002" to 0.010", preferably 0.005" to 0.006". The distal tip of the Nitinol wire corresponding to the free end of the distal turn 316, preferably, carries an enlargement, as for example a small ball or flattened tip 310 so as to prevent puncture of the membrane 311 by the wire during operation of the device and so as to decrease friction of the tip 310 against the wall of the lumen 306 of the first flexible elongate tubular member 302 out of which the expansile mechanism 309 is pushed as hereinafter discussed. The ball 310 may be formed by a suitable method such as arc welding, soldering, applying a polymer to the wire or folding the tip of the wire.

The deployment means or mechanism 308 includes a push-pull element or member 317 preferably in the form of a wire 317, with proximal and distal extremities 318 and 319 which is slidably disposed in and extending through the first or main lumen 306. The push-pull element 317 is formed of a suitable material such as stainless steel and has a suitable diameter as for example from 0.005" to 0.030", preferably 0.010". The expansile member 309 and the push-pull element 317 may be separately constructed and subsequently joined together utilizing one of several different methods. The two may be bonded or soldered together. Preferably, in order to provide for optimal torque, the stainless steel wire 317 is ground to provide a tapered portion 317a formed on the distal end 319. The tapered portion 317a is inserted into one end of an elongate member, often called a hypotube 320 made of an appropriate material such as stainless steel and adhesively bonded therein using an appropriate adhesive 325 such as Loctite™. The proximal end 318 of the Nitinol wire expansile member 309 is similarly inserted and bonded into the opposite end of the hypotube 320. The stainless steel hypotube 320 may be of an appropriate length, such as from 2 to 15 cm, preferably 4.5 cm. It may have an outer diameter ranging from 0.005" to 0.030", preferably 0.010" and an inner diameter ranging from 0.003" to 0.010", preferably 0.006".

Alternatively, both the push-pull wire 317 and the expansile mechanism 309 can be formed from a single piece of Nitinol wire in which case, in order to provide optimal pushability, torquability and column strength of the push-pull wire 317, two alternative techniques are utilized. First, a Nitinol wire diameter of approximately 0.010" is used by grinding down the distal end 319 to a diameter suitable for subsequent formation of the expansile member 309.

A second technique utilizes a Nitinol wire having a diameter suitable for formation of the expansile mechanism 309. In such case, the push-pull wire 317 is covered with a suitable polymer jacket, preferably made of polyimide and having an diameter of approximately 0.005" to 0.0101". The polymer jacket is thicker at the proximal end 318, necked down at the distal end 319 of the push-pull wire 317 and secured to the push-pull wire 317 at distal and proximal ends by a suitable adhesive such as Loctite™.

As shown in FIG. 18 the proximal end 318 of the push-pull wire 317 extends out of the proximal extremity 303 of the first flexible elongate tubular member 302 so that the deployment means can be operated by the human hand as hereinafter described.

It should also be appreciated that push-pull elements or mechanisms, other than a push-pull wire, can be utilized to deploy and de-deploy the expansile member and the expansile assembly.

A stop mechanism or means 321 is provided to control the range of movement or travel of the push-pull wire 317 during deployment and de-deployment of the expansile assembly 307. The stop mechanism 321 comprises first and second, slidable nested or coaxially mounted stop tubes 322 and 323 formed of an appropriate material such as plastic or stainless steel. The distal end of the first stop tube 322 carries a bushing 324. The bushing 324 is secured to the distal end of the first stop tube 322 by suitable means such as an adhesive (not shown). The proximal end 318 of the push-pull element 317 is affixed to the first tube by suitable means such as an adhesive. The push-pull element 317 with the first tube 322 affixed thereto and the bushing 324 carried thereby is movable longitudinally of the second tube 323 which has its distal extremity secured to the proximal extremity 303 of the elongate tubular member 302. It is movable from a forward most position with the bushing 324 in engagement with the proximal end 303 and a rearwardmost position in engagement with an annulus 326 mounted in the proximal extremity of the second tube 323 by suitable means such as an adhesive and through which the first tube 322 slidably extends. The lengths of the first and second tubes 322 and 323 are selected so that the travel between the forwardmost and rearwardmost positions ranges between 2 cm and 10 cm.

The expansile assembly 307 also includes a deformable, flexible membrane 311 which is carried by, and as shown, can be secured to the distal extremity 304 of the first flexible elongate tubular member 302 as hereinafter discussed. Since it is desired that this membrane 311 be very flexible it has a wall thickness ranging from 0.001" to 0.015" and preferably about 0.004". It can be formed of any suitable flexible material such as an elastomeric or a non-elastomeric material including latex and silicone. The membrane 311 can also be made of an impermeable or a permeable material providing for multiple uses of the device. A satisfactory membrane 311 can be made of Chemoprene™ or one of the polyurethane elastomers such as Polyblend™ having a shore hardness durometer of 30 to 70 A, and preferably 55 A, Tecoflex™ having a shore hardness durometer of 60 to 100 A or Pellathane™ having a shore hardness durometer of 70 to 100 A. Alternatively the membrane 311 can be made of multiple layers including a central Polyblend™ layer having a thickness of approximately 0.005" to 0.010" and a thin outer Tecoflex™ layer having a thickness of approximately 0.0005". This layered membrane 311 is made by dipping the Polyblend™ in a Tecoflex™ solution, for example a Tecoflex™ 85 A solution. As shown, the membrane 311 is substantially impermeable to blood and other liquids. It is formed as a tubular sock 333 which has an elongate generally cylindrical configuration with one closed end 329 and the other end circumscribed by an opening 331 which is defined by a rim 332 of the same material. The tubular sock 333 has an appropriate length, as for example ranging from 2–15 mm, preferably 7 mm. When the membrane 311 is made from Polyblend™, typically supplied in a tubular form and cut into lengths of appropriate dimensions with both ends open, the closed end 329 of the membrane 311 is formed by dipping one open end of the Polyblend™ into a Tecoflex™ solution, preferably 10% by weight of 85 A Tecoflex198 , to provide a sealing plug 327. The rim 332 of the membrane 311 can be circumferentially secured to the distal extremity 304 of the first flexible elongate tubular member 302 in a suitable manner such as by the Loctite 454™ adhesive (not shown).

A length of stainless steel hypotube 328 has one end secured to the distal end 304 of the first flexible elongate tubular member 302 (see FIG. 18) using an appropriate adhesive such as Loctite 406™. The hypotube 328 has an appropriate length ranging from 2 mm to 10 mm, preferably 5 mm, and is secured to the first flexible elongate tubular member 302 and extends distally of the same by approximately 2–8 mm. The rim 332 of the membrane 311 is affixed exteriorly of the stainless steel hypotube 328 by an adhesive (not shown), preferably, distal to the point at which the hypotube 328 is secured to the first flexible elongate tubular member 302 and with the closed end 329 of the membrane 311 oriented distally thereon as shown in FIG. 18. As such, a portion of the membrane 311 distal to the rim 332 overlies the steel hypotube 328 and is non-adherent thereto. It should be appreciated if desired that the rim 332 can be secured directly to the outer surface of the distal extremity 304. In either arrangement, the membrane 311 assumes a sock-like conformation as shown in FIG. 18. Alternatively, the rim 332 of the membrane 311 may be secured interiorly within the hypotube 328 or, if the hypotube 328 is not utilized, within the first or main lumen 306 of the first flexible elongate tubular member 302. In addition, the membrane 311 may be secured to the Nitinol wire proximal to the expansile member 309.

The impermeable membrane 311 of the expansile assembly 307 can be caused to assume various configurations including a planar disk-like configuration as shown by the dotted-line position in FIG. 18. This is accomplished by operation of the deployment mechanism 308 to move the push-pull element 317 distally to urge the expansile member 309 distally out of the lumen 306 into the membrane 311. The operator can assist deployment by applying a slight rotation to the push-pull element 317 as it is moved distally. As soon as the expansile member 309 clears the first lumen 306, it begins to expand into its shape memory, predetermined configuration. The distal turn 316 of the expansile member 309 in the form of a coil operates to expand the membrane 311 initially to a small degree. This initial process avoids sudden gross distortion of the membrane 311. As the expansile member 309 moves distally out of the lumen 306 and expands into the membrane 311, the non-adherent portion of the membrane 311 distal to the rim 332 preferentially begins to move and assume the planar configuration because of the lubricious surface of the stainless steel hypotube 328. Expansion proceeds with the middle turn 314 forming a coil and causing the membrane 311 to expand to its desired size, approximately 12 French. The proximal turn 313 forming a coil then centralizes and stabilizes the configuration so that the push-pull element 317 is centered with respect to the middle turn 314 and the fully expanded membrane 334. During expansion of the expansile member 309 the membrane 311 covering the coil 312 constrains the coil 312, thus exerting counteractive or countervailing contractile forces on the expanding coil 312 which is seeking its memorized, bi-conical, free shape or configuration 312. Thus, the membrane 311 does not expand passively. Rather, the expanding coil 312 forcibly expands the membrane 311 to cause the non-planar turns 313, 314 and 316 of the coil 312 to assume a substantially planar or disk-like configuration with the membrane 334 being taut and disposed on opposite sides of the expansile mechanism 309 to form an expansile assembly 307 which when expanded is generally perpendicular to the longitudinal axis of the first flexible elongate tubular member 302. The expansile mechanism 309 when deployed is sufficiently rigid so as to provide a supporting framework for the membrane 311 to keep it taut.

It should be appreciated that other embodiments may be utilized employing super-elastic expansile members with various memorized configurations. In addition, as hereinbefore discussed, different membrane materials may be utilized in order to construct permeable or impermeable assemblies for different functions. The predictability of countervailing, expansile forces and resistive, membrane forces enables the construction of expansile assemblies with predetermined, deployed configurations. In addition, instead of sliding a push-pull wire, the Nitinol member can be secured to a wire which remains stationary. In such an embodiment, the expansile member and wire are sheathed within an elongate tubular member which has a sock-like membrane secured to the distal end thereof and whence the member is deployed into the membrane by sliding the sheath proximally.

Operation and use of the device 301 is very similar to that described for the embodiment of the closure device 21 with the following differences. The expansile device 301 shown in FIGS. 18–19 is not used with biological sealants. Thus, after bringing the expansile assembly 307 into contact with the distal end of the puncture 106, a proximal force of tension or traction is maintained on the expansile assembly 307 for a predetermined period of time ranging from 2 minutes to several hours, preferably 30 minutes to 1 hour, until the puncture 106 is sealed. Release of the tension is followed by moving the expansile assembly 307 from the deployed or expanded position to the de-deployed or contracted position after which the device 301 may be removed as hereinbefore described.

A second difference is that the radio-opacity of the expansile mechanism 309 is determined by the configuration of the coil 312. When it is in the unconstrained, memorized, bi-conical configuration, the coil 312 is not fluoroscopically visible due to the small size of the individual turns of the Nitinol wire and the non-planar configuration. When the expansile mechanism 309 assumes the flat disk-like shape within the membrane 334 the cumulative densities of the Nitinol turns can be fluoroscopically visualized. As hereinbefore discussed, this too is an easy method of ascertaining or confirming formation of a good seal between the expansile assembly 307 and the wall 103 of the vessel 107.

Furthermore, the low profile of the device 301 affords the ability to reenter the vessel 107 with the introducer sheath 111 if there has been inadequate occlusion and bleeding continues or other complications ensue. For example, let it be assumed that the operator believes the puncture 106 is sealed after removal of the sheath 111 and he therefore de-deploys the expansile assembly 307 as hereinbefore described. If, after so doing, he observes continued bleeding from the puncture 106, the operator can reenter the vessel 107 by releasing tension, pushing the first flexible elongate tubular member 302 distally and reinserting the sheath 111 into the vessel 107 over the first flexible elongate tubular member 302. The operator can also reenter the vessel for additional medical purposes if necessary. The same approach applies if the membrane 311 breaks or the expansile assembly 307 otherwise malfunctions. In this case the sheath 111 is replaced as hereinbefore described and the malfunctioning expansile device 301 is expeditiously replaced.

A tension applicator or catheter retention means 335 is provided which engages the elongate tubular member 302 and serves to releasably place tensioning forces on the elongate tubular member 302 to maintain engagement of the deployed expansile assembly 307 against the vessel wall 103 having a puncture 106 therein and to free the operator's hands from having to hold the device 301 after it is correctly deployed in the puncture 106. The catheter retention means 335 provides a predetermined and substantially constant force in a proximal direction on the expansile member 309 over a range of motion or positions of the flexible elongate tubular member 302 which may occur as a result of patient movement or initial positioning.

The tensioning device 335 is shown in FIGS. 20–23 and consists of a fixture 336 or bottom portion which is constructed of a suitable material such as clear plastic and comprises a base plate 337 having an appropriate shape and size, as by way of example a pear-shape and size, as shown in FIG. 20 and adapted to rest on the skin 101 overlying the puncture 106 in the wall 103 forming the lumen 107. The fixture 336 further comprises anterior and posterior walls 338 and 339 which extend upwardly, preferably at approximately right angles from the surface of the base plate 337. The posterior wall 339 has an outer face 342 that is straight and an inner face 343 that is inclined. The anterior wall 338 also has inner and outer faces 344 and 346 that are straight. A swingable arm or top portion 347 is hingedly or pivotally mounted to the top of the posterior wall 339 of the base portion 336 for movement between open and closed positions with respect to the base portion 336. In the open position, the top portion 347 may assume an angle of up to 180 degrees, preferably 45 degrees, with respect to the base portion 336. In the neutral or closed position, the top portion 347 substantially overlies and is parallel to the base portion 337. As hereinafter described however, in the closed position, the top portion 347 is also capable of at least 0.5 cm of additional travel or motion in both closed and open directions, both towards and away from the base portion 336, respectively.

The arm 347 is hinged and biased or yieldably urged towards the open position, away from the skin of the patient, by spring means capable of providing a predetermined and substantially constant tensioning force over a range of positions. The top and bottom portions 347 and 336 of the tensioning device 335 can be constructed as one piece which incorporates a living hinge 348 formed by scoring or placing a groove in the plastic. Alternatively, a metal or other hinge can be utilized to join separate top and bottom portions. A constant force spring, such as a coil spring 349 capable of providing an appropriate constant force of tension is preferably utilized as hereinbefore discussed. It should be appreciated that any type of spring capable of providing the aforementioned constant force of tension can be used, as, by way of example, flat, leaf, spiral, helical, disk and volute springs.

As shown in FIG. 20, catheter clamping or grasping means in the form of grasping members 351 are carried by the arm 347 and are movable between open or release, and closed or clamping positions. The grasping members 351 are in the form of serrated pads constructed of an appropriate material, such as plastic, rubber or metal. The grasping members 351 are carried by the distal extremities of flexible elongate curved spring members or grasping arms 352. The arms 352 may be constructed of a suitable spring material such as plastic or metal and are disposed in a recess 350 of the casing of the top portion 347. The proximal extremities of the spring arms 352 are disposed on opposite sides of spaced apart pins 352 mounted so that the proximal extremities are biased towards each other into the clamping position.

Means are provided for overcoming the bias of the spring arms 352 and consists of flanged actuator buttons 354 slidably mounted in holes. Actuator arms 355 are secured to the buttons 354 and extend one behind the other to engage the opposite spring arm 352 (see FIG. 21) so that the spring arms 352 can be moved apart to move the grasping members 351 to the open position.

The fixture and arm portions 337 and 347 may be formed with slots 356 and 357 which are in alignment when the arm 347 is in the closed position and in which the first elongate tubular member 302 or body 362 is disposed when being grasped by the grasping members 351.

Operation of the tension applicator 335 may now be described in conjunction with FIGS. 21–23. By placing the fixture 336 against the patient's skin and, as shown in FIGS. 22–23, urging or forcing the arm 347 towards the fixture 336 until it comes into apposition with the base plate 337 and opening the spring arms 352 in order to grasp the first flexible elongate tubular member 302 or elongate tubular body 362, the tensioning device 335 can be set or activated whence it maintains a suitable, constant proximal force of tension, preferably within a range of 0.25 to 3 pounds, over a range of motion. The force applied to the first flexible elongate tubular member 302 attempts to withdraw the member 302 from the puncture 106 in the wall 103 of the vessel 107 so that the expansile device 302 is retained in engagement with the wall 103 of the vessel 107.

Indicator marks in the form of arrows 358 are placed on the fixture 336 and the arm 347 so that the marks are aligned with one another when the tensioning means 335 is correctly positioned and activated in the neutral, closed position as hereinbefore described. Alternatively, visualization through the clear plastic base plate 337 can serve as indicator means.

It should be appreciated that other embodiments of the tension applicator or tensioning device may be utilized in the present invention without departing from the novelty and the intended uses thereof. For example, the grasping means can be comprised of asymmetrical members and arms, similar to a pin vise or clamp. In such an embodiment one grasping arm is slidably disposed within another and can be spring loaded or otherwise biased into a position in which one grasping member is apposed with the other grasping member. Alternatively, two grasping arms may be constructed from a single arm which has been partially split along its longitudinal axis, providing arms that splay apart. Grasping members may also be comprised of clamps that snap or roll into closed positions. Similarly, the arm may have a length that is shorter than the bottom portion and beyond which the grasping members and arms extend. It should also be appreciated that the tension applicator 335 can be used with other catheters.

The tensioning device 335 with its indicators also serve to confirm formation of a good, occlusive seal of the puncture 106 with the expansile assembly 307. The deployed expansile assembly 307 withstands the aforementioned proximal force or tension and in so doing maintains the occlusive seal unless the deployed coil 312 and disk-shaped membrane 334 change configurations. For example, if the membrane 311 breaks, the coil 312 once again assumes its memorized bi-conical configuration 312 which cannot maintain a high tensile force and is incompatible with puncture occlusion. As tension is lost the indicator on the tensioning device 335 is activated, alerting the operator to the release of the predetermined force of tension and lack of an adequate seal.

Figure 24:
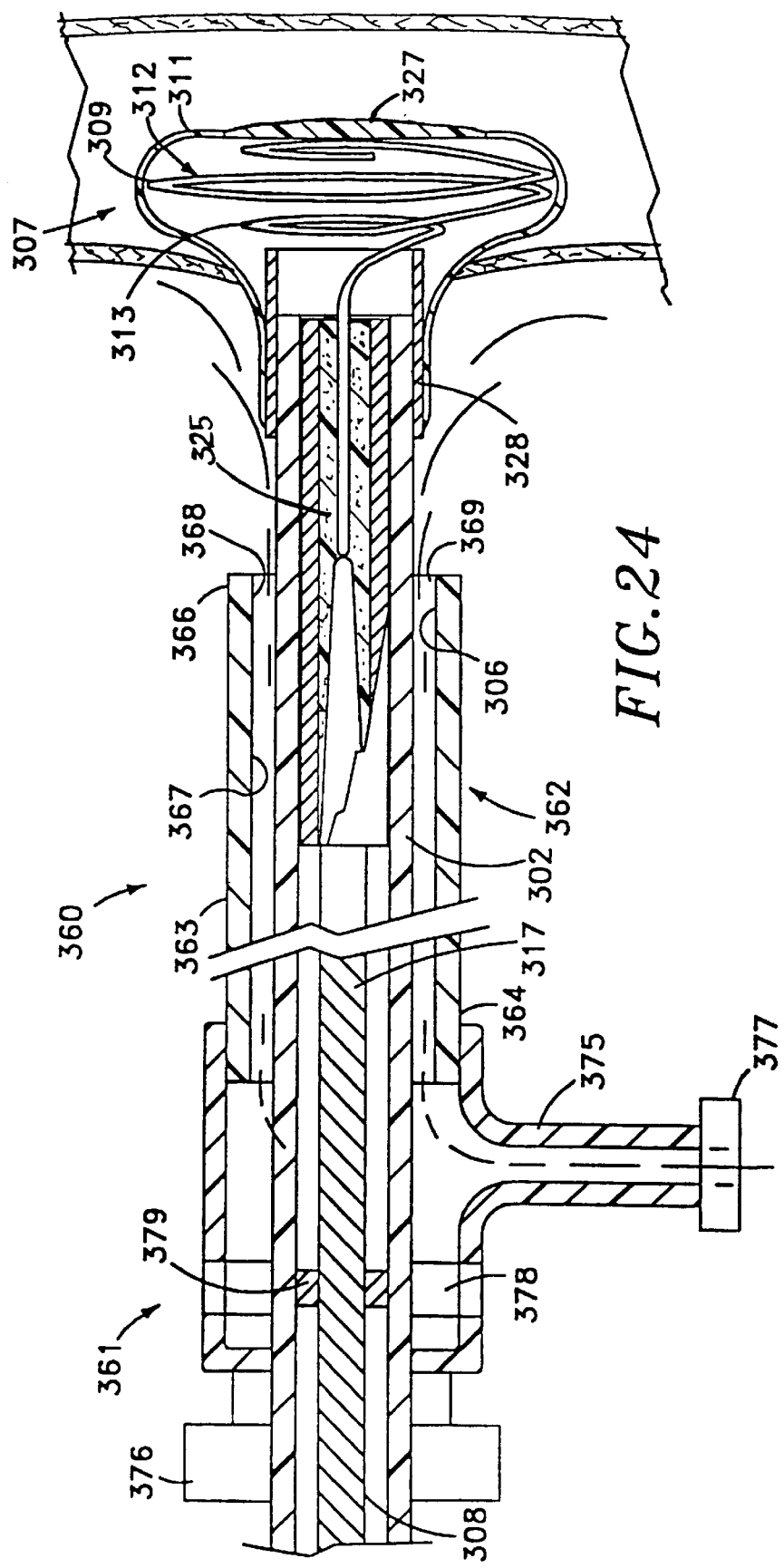
FIG. 24 is a cross-sectional view of the device of FIG. 18 with one embodiment of the biological sealant introducing means.

Another embodiment of the expansile device is shown in FIG. 24. The expansile device 360 is very similar to that shown in FIG. 18 with the principal difference being that, in addition, it provides means for introducing a biological sealant into the puncture proximal to the expansile mechanism to seal the puncture. Thus all the parts of the expansile device 301 that are present in the expansile device 360 carry the same numbers. The biological sealant introducer means 361 is carried by a flexible elongate tubular body 362 comprising first and second flexible elongate tubular members 302 and 363. The first flexible elongate tubular member 302 is as hereinbefore described. The second flexible elongate tubular member 363 is formed of suitable plastic material, preferably an extruded thermoplastic elastomer such as Pebax™ having a shore hardness durometer of 50 D or 72 D. The second flexible elongate tubular member 363 has proximal and distal extremities 364 and 366, extends along a longitudinal axis and has an inner wall 367 defining a lumen 368 extending from the proximal 364 to the distal extremity 366. The lumen 368 has a diameter greater than the outer diameter of the first flexible elongate tubular member 302. The first flexible elongate tubular member 302 is disposed or nested within the lumen 368 of the second flexible elongate tubular member 363 thereby defining a first, circumferential or annular space 369 between the outer surface of the first flexible elongate tubular member 302 and the inner wall 367 of the second flexible elongate tubular member 363. The distal extremity 366 of the second flexible elongate tubular member 363 terminates proximal to the distal extremity 304 of the first flexible elongate tubular member 302 and adjacent to the expansile mechanism 309.

The second flexible elongate tubular member 363 is of a suitable size, as for example an outer diameter ranging from 0.020" to 0.050", an inner or lumen diameter ranging from 0.015" to 0.040" and has a suitable length as for example 10–160 centimeters. As hereinbefore discussed, the distal extremity 366 of the second flexible elongate tubular member 363 terminates proximal to the distal extremity 304 of the first flexible elongate tubular member 302 and adjacent to the expansile mechanism 309, as for example 1–15 millimeters up to several centimeters proximal.

Proximal adaption for sealant introduction into the flexible elongate tubular body 362 includes appropriate tee or wye adapters. Preferably, as shown in FIG. 24, a tee adapter 375 has one end fixed to the proximal extremity 364 of the second flexible elongate tubular member 363 using a suitable adhesive. The second end of the tee adapter 375 carries a compression fitting 376 in order to accommodate the proximal end 303 of the first flexible elongate tubular member 302 which is disposed within and extends proximally out of the tee adapter 375. The compression fitting 376 provides a leakproof connection between the first and second flexible elongate tubular members 302 and 363 and enables removal of the second flexible elongate tubular member 363 while the first flexible elongate tubular member 302 is maintained in the deployed position. Introduction of sealants is accomplished via a fluid port 377 which communicates with the proximal end 364 of the second flexible elongate tubular member 363 as shown in FIG. 22. An alignment window 378 in the tee adapter 375 is provided which is used to visually align a marker 379 on the proximal extremity 303 of the first flexible elongate tubular member 302 or on the proximal extremity 318 of the push-pull wire 317 so that the distal extremity 366 of the second flexible elongate tubular member 363 is appropriately positioned proximal to the distal extremity 304 of the first flexible elongate tubular member 302 and adjacent to the expansile mechanism 309 as hereinbefore described.

Operation and use of the device 360 is similar to that described for the expansile device 301 except for the ability to introduce biological sealants with the device 360. As soon as it has been established that a good seal has been formed between the occlusion assembly 307 and the wall 103 adjacent the puncture the operator can introduce the constituents of the biological sealant into the fluid port 377 of the adapter 375 hereinbefore described. The sealant is then introduced into the proximal end 364 of the second flexible elongate tubular member 363 into the first space 369 between the outer surface of the first flexible elongate tubular member 302 and the inner wall 367 of the second flexible elongate tubular member 363, thence exiting proximal to the distal extremity 304 of the first flexible elongate tubular member 302 and adjacent to the expansile mechanism 309. The remainder of the operation of the device 360 is as hereinbefore described in conjunction with the use of the device 21 and the device 301.

Figure 25:
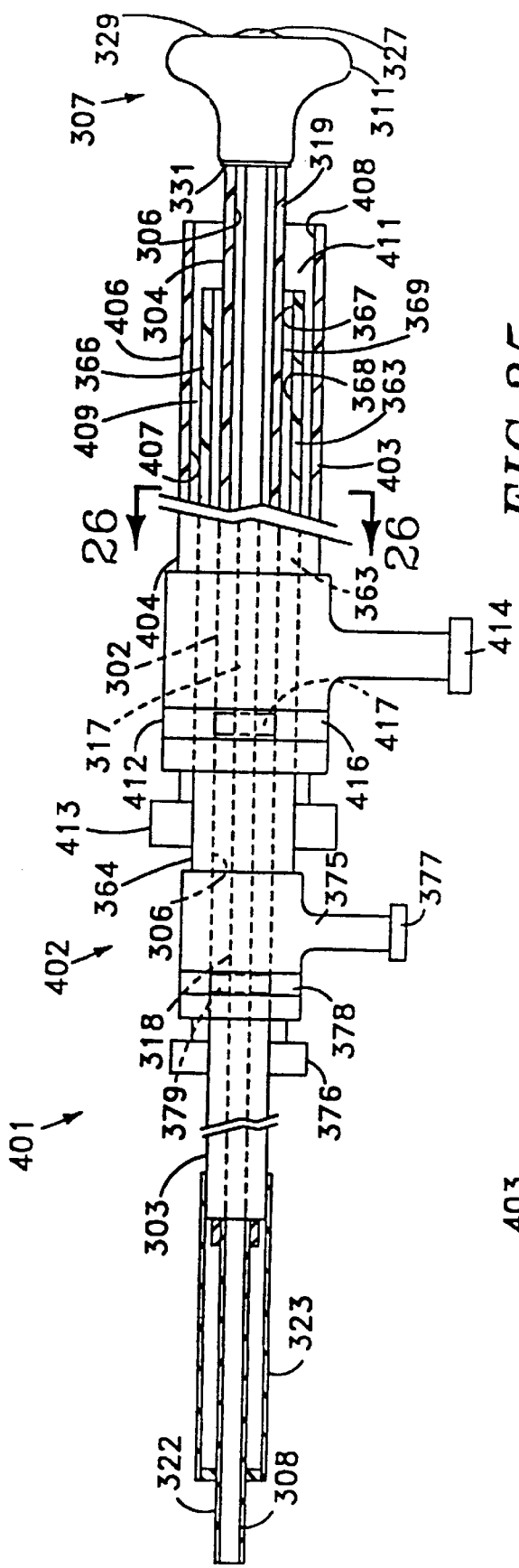
FIG. 25 is an side-elevational view partially in section of another embodiment of the expansile device of the present invention shown with its biological sealant introducing means.
Figure 26:
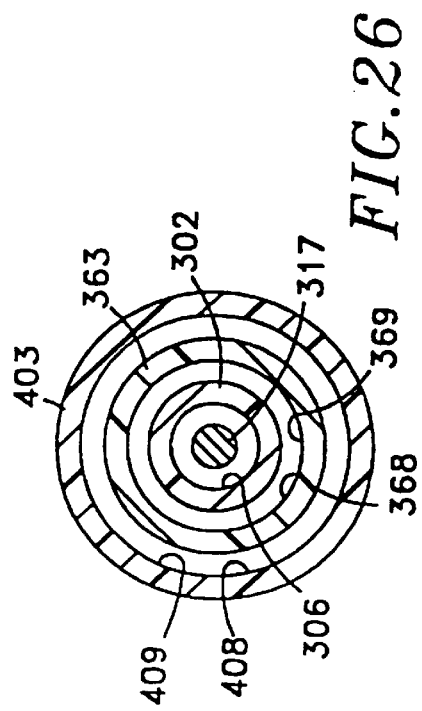
FIG. 26 is a cross-sectional view taken along the line 26—26 of FIG. 25.

Another embodiment of a expansile device incorporating the present invention is shown in FIGS. 25–26. The expansile device 401 is very similar to that shown in FIG. 24 with the principal difference being in the biological sealant means utilized in the device 401. Thus all of the parts of the expansile device 360 that are present in the expansile device 401 carry the same numbers. The biological sealant means 402 is also similar to that shown in FIG. 24 with the principal difference being that the flexible elongate tubular body 362 further includes a third flexible elongate tubular member 403 formed of suitable plastic material, also preferably an extruded thermoplastic elastomer such as Pebax™ having a durometer of 63 D or 72 D. The third flexible elongate tubular member 403 has proximal and distal extremities 404 and 406, extends along a longitudinal axis and has an inner wall 407 defining a lumen 408 extending from the proximal 404 to distal extremity 406 and having a diameter greater than the outer diameter of the second flexible elongate tubular member 363. The second flexible elongate tubular member 363 is nested or disposed within the lumen 408 of the third flexible elongate tubular member 403 thereby defining a second, circumferential or annular space 409 between the second flexible elongate tubular member 363 and the inner wall 407 of the third flexible elongate tubular member 403. The distal extremity 406 of the third flexible elongate tubular member 403 terminates distal to the distal extremity 366 of the second flexible elongate tubular member 363 and proximal to the distal extremity 304 of the first flexible elongate tubular member 302 thereby defining an annular distal mixing chamber 411 between the first flexible elongate tubular member 302 and the inner wall 407 of the third flexible elongate tubular member 403.

The third flexible elongate tubular member 403 is of a suitable size, as for example an outer diameter ranging from 0.030" to 0.070", and has a suitable length as for example 10–160 centimeters. As hereinbefore discussed, the distal extremity 406 of the third flexible elongate tubular member 403 terminates distal to the distal extremity 366 of the second flexible elongate tubular member 363, as for example from 1–15 millimeters distal, preferably 5 millimeters, thus creating the distal mixing chamber 411. The distal extremity 406 of the third flexible elongate tubular member 403 also terminates proximal to the distal extremity 304 of the first flexible elongate tubular member 302 and adjacent to the expansile mechanism 309, as for example 1–15 millimeters up to several centimeters proximal. In order to affect this configuration, the second flexible elongate tubular member 363 may be of a suitable length that is slightly shorter than the length of the second flexible elongate tubular member 363 in device 360.

Proximal adaption for sealant introduction into this triple flexible elongate tubular member body is provided so that either the second flexible elongate tubular member 363 or the second and third flexible elongate tubular members 363 and 403 can be reversibly disengaged and removed. Removing the second flexible elongate tubular member 363 provides access to a larger space between the first and third flexible elongate tubular members 302 and 403 in order to provide for more reliable aspiration attempts. Removing both the second and third flexible elongate tubular members 363 and 403 provides for use of the isolated expansile device 301 as hereinbefore discussed, and also permits cleaning of the removed tubular members as necessary.

The proximal adaption for the device 401 includes appropriate tee or wye adapters as hereinbefore described. The proximal adaption 375 for the second flexible elongate tubular member 363 is similar to the proximal adaption 375 for the second flexible elongate tubular member 363 in device 360. The third flexible elongate tubular member 403 carries similar proximal adaption 412 in the form of a tee adapter 412, compression fitting 413 and a fluid port 414 so that, as hereinbefore discussed, the second flexible elongate tubular member 363 can be disposed or nested within the third flexible elongate tubular member 403 with a proximal seal between the two members that is fluid-tight. A second sealant or component thereof can be introduced into the fluid port 414 of the compression fitting 413 on the third flexible elongate tubular member 403 as hereinafter discussed.

In addition, the proximal adapter 412 of third flexible elongate tubular member 403 carries an alignment window 416 in order to permit the operator to visually align a marker 417 on the second flexible elongate tubular member 363 within the window 416 so that during use the second and third flexible elongate tubular members 363 and 403 are appropriately positioned with respect to one another. It should be appreciated that second and third flexible elongate tubular members 363 and 403 can be constructed as a single unit whereby only the unit is capable of being inserted and removed over the first flexible elongate tubular member.

Operation and use of the device 401 is similar to that described for the expansile device 360 except for use of the biological sealant means 402 in the device 401. As soon as it has been established that a good seal has been formed between the occlusion assembly 307 and the wall 103 adjacent the puncture the physician can introduce the constituents of the biological sealant into the fluid port 377 of the adapter 375 on the proximal end 364 of the second flexible elongate tubular member 363 into the first space 369 and into the fluid port 414 of the adapter 412 on the proximal end 404 of the third flexible elongate tubular member 403 into the second space 409 respectively, causing the constituents to travel separately, distally into the distal mixing chamber 411 where they are well mixed and whence the mixed sealant exits proximal to the distal extremity 304 of the first flexible elongate tubular member 302 and adjacent to the expansible mechanism 309. The remainder of the operation of the device 401 is as hereinbefore described in conjunction with the use of the device 21.

Another embodiment than expansile device incorporating the present invention is shown in FIGS. 27–30. The expansile device 418 is also very similar to that shown in FIG. 24 with the principal difference being in the biological sealant means 419 utilized in the device 418. Thus all of the parts of the expansile device 360 that are present in the expansile device 418 carry the same numbers.

The second flexible elongate tubular member 363 of the device 418 is provided with an additional or second lumen 425 which may be half-circular in cross-section, is laterally disposed and also extends from the proximal extremity 364 to the distal extremity 366 of the second flexible elongate tubular member 363 as shown in FIG. 27. In order for the second flexible elongate tubular member 363 to carry the second lumen 425, the first lumen 368 may also be laterally disposed. The second lumen 425 has a suitable chord length ranging from 0.020" to 0.040".

The second lumen 425 of the device 418 may be utilized for introducing biological sealants as hereinbefore described in conjunction with the device 360. The second lumen 425 can also be used for aspiration attempts, to verify formation of a good seal between the expansile assembly 307 and the wall 103 of the vessel 107 has hereinbefore described in conjunction with the device 21.

The expansile device 418 is also provided with a third flexible elongate member 430 having proximal and distal extremities 431 and 432 and extending along a longitudinal axis. Shown in FIGS. 27–28 and FIG. 30, the third flexible elongate member 430 is sized and shaped to be reversibly, frictionally disposed within the second lumen 425 of the second flexible elongate tubular member 363 and has a length substantially equal to the length of the second flexible elongate tubular member 363.

The third flexible elongate member 430 is similarly formed of a suitable plastic material such as Pebax™ and is solid in construction, as shown in FIG. 28, so that it functions as an obturator for the second lumen 425 of the second flexible elongate tubular member 363, thus keeping the same unobstructed until ready for use.

There is provided an alternate third flexible elongate member 433 which is similarly sized and shaped and functions as a biological sealant introducer means. As shown in FIGS. 27 and 30, this alternate third flexible elongate member 433 carries first and second lumens 434 and 436, each extending from the proximal to the distal extremity 431 and 432 of the alternate third flexible elongate member 433. A mixing chamber 437 contiguous with and created by the distal confluence of the first and second lumens 434 and 436 is carried by the distal extremity 432 of the third flexible elongate member 433. Alternatively, the third flexible elongate member 433 can be without the aforementioned distal confluence of lumens and, in place thereof, have a length slightly shorter than that of the second flexible elongate tubular member 363 so that a mixing chamber 437 is created within the distal end 366 of the second flexible elongate tubular member 363.

Proximal adaption 438 for sealant introduction into this third flexible elongate member 433 is provided as shown in FIG. 27. The proximal extremity 431 of the third flexible elongate member 433 carries a fitting or adapter 438 having two or more fluid ports 439 in alignment with the first and second lumens 434 and 436 of the third flexible elongate member 433. The fitting 438 is constructed out of a suitable material such as plastic or nylon, by way of example, polycarbonate or Isoplast™, and is bonded to the third flexible elongate member 433 by an appropriate adhesive. Alternatively, the adapter 438 can be constructed of Pebax™ 82 D, and be heat fused to the proximal end 431 of the third flexible elongate member 433. It should be appreciated that the adapter 438 may be constructed so as to be reversibly connected to the third flexible elongate member 433.

Operation and use of the device 418 is similar to that hereinbefore discussed in conjunction with the device 401. Constituents of biological sealants are introduced proximally into the adapter 438 and thence into the first and second lumens 434 and 436 causing the constituents to travel separately, distally into the distal mixing chamber 437 where they are well mixed and whence the mixed sealant exits proximal to the distal extremity 304 of the first flexible elongate tubular member 302 and adjacent to the expansile mechanism 309.

Alternately, as shown in FIGS. 31–32, a third flexible elongate tubular member 450 is provided which, other than being tubular in shape, is similar in construction to the alternate third flexible elongate members hereinbefore discussed. This third flexible elongate tubular member 450 is also sized to be frictionally disposed within the second lumen 425 of the second flexible elongate tubular member 363 in which case the area in the second lumen 425 of the second flexible elongate tubular member 363 surrounding the third flexible elongate tubular member 450 is used as a second space 451 into which biological sealants are introduced as hereinafter discussed.

Proximal adaption for sealant introduction into the second lumen 425 of the second flexible elongate tubular member 363 and the third flexible elongate tubular member 450 is provided as shown in FIG. 31. The proximal extremity 364 of the second flexible elongate tubular member 363 carries a fitting or adapter 452 constructed in a manner similar to that hereinbefore discussed. The adapter 452 has proximal and distal ends 453 and 454 and carries a variably-shaped lumen 456 extending therethrough. The distal end 454 of the adapter lumen 456 is sized, configured and aligned with the second lumen 425 of the second flexible elongate tubular member 363. The proximal end 453 of the adapter lumen 456 is circular in cross-section and is sized so as to frictionally accept the third flexible elongate tubular member 450. A fluid port 457 is connected to the adapter lumen 456. As shown in FIG. 31, the proximal end 431 of the third flexible elongate tubular member 450 also carries a fluid port 458. The third flexible elongate tubular member 450 is of a slightly shorter length than that of the second flexible elongate tubular member 363 in order to create the distal mixing chamber 437 as hereinbefore discussed. Operation and use is as hereinbefore described.

Alternatively, instead of utilizing a third flexible elongate member the second flexible elongate tubular member of the expansile device is provided with a third lumen (not shown) extending from the proximal to the distal extremity and. A mixing chamber contiguous with and created by the distal confluence of the second and third lumens and is carried by the distal extremity of the second flexible elongate tubular member. Proximal adaption for sealant introduction and a handle assembly can be utilized as hereinbefore discussed. Operation and use is as hereinbefore described.

Another embodiment of an expansile device incorporating the present invention is shown in FIGS. 33–34. The expansile device 501 is similar to that shown in FIGS. 18, 24 and 25 with the principal difference being in the biological sealant introduction means utilized in the device 501. Thus all the parts of the expansile device 301 that are present in the expansile device 501 carry the same numbers. Solid biological sealant introducer means 502 is provided by a second elongate tubular member 503 having proximal and distal extremities 504 and 506, a longitudinal axis and first and second lumens 507 and 508 extending from the proximal extremity 504 to the distal extremity 506 of the second elongate tubular member 503. The distal extremity 506 of the second elongate tubular member 503 terminates proximal to the distal extremity 304 of the first elongate tubular member 302 and adjacent to the expansile member 309, the first elongate tubular member 302 being disposed in the second lumen 508 of the second elongate tubular member 503.

The second elongate tubular member 503 is preferably flexible and formed of a suitable plastic material, preferably an extruded Pebax™, Elf Atochem™ or other suitable thermoplastic elastomer having a shore hardness durometer of 50 D or 72 D. The coil or crush strength of the second elongate tubular member 503 is great enough so that it withstands the force of the grasping members 351 of the tensioning device 335 without being functionally deformed or compromised as hereinbefore described. The first elongate tubular member 302 is retained and fixed in the second lumen 508 of the second elongate tubular member 503 by suitable adhesive means as hereinafter described.

The second elongate tubular member 503 is of a suitable size, as for example having an outer diameter ranging from 0.050" to 0.090", preferably approximately 0.072", a first lumen 507 having a diameter ranging from 0.020–0.060", preferably 0.040", a second lumen 508 having a diameter ranging from 0.015–0.040", preferably 0.020" and a suitable length as for example ranging from 10–100 cm and preferably being approximately 30 cm.

The distal extremity 506 of the second elongate tubular member 503 carries a tip 509 having a circumference 511 at least a portion of which lies in a plane forming an angle with the longitudinal axis of the second elongate tubular member 503 which is greater than 90 degrees. This is preferably accomplished by providing the tip 509 with a bevel so that the second lumen 508 of the second elongate tubular member 503 terminates distally of the first lumen 507 of the second elongate tubular member 503, preferably 3–8 mm distally thereof as hereinafter described. As hereinbefore described, the distal extremity 506 of the second elongate tubular member 503 terminates proximal to the distal extremity 304 of the first elongate tubular member 302 and adjacent to the expansile member 309 by approximately 5–15 mm. Thus, the tip 509 terminates approximately 3–8 mm proximal to the steel hypotube 328 carried by the distal extremity 304 of the first elongate tubular member 302.

Proximal adaption for solid sealant introduction into the first lumen 507 of the second elongate tubular member 503 includes an appropriate wye hub or adaptor 521 carried by the proximal extremity 504 of the second elongate tubular member 503. The adaptor 521 is constructed of an appropriate plastic material such as machined Delrin or other acetal or polycarb material. As shown in FIG. 33, a first arm or end 522 of the adaptor 521 is provided having a lumen 523 in alignment with the second lumen 508 of the second elongate tubular member 503. The first arm 522 is also provided with a proximally extending annular ring, 524, recess or rim in alignment with the lumen 523 of the first arm 522. The proximal extremity 303 of the first elongate tubular member 301 extends proximally from the second lumen 508 of the second elongate tubular member 503 and thence out of the lumen 523 of the first arm 522 and into the ring 524. The second stop tube 323 of the first elongate tubular member 301 is seated within the ring 524 and secured to the adaptor 521 by appropriate adhesive means thereby forming a fluid-tight seal and fixing the first elongate tubular member 301 in relation to the second elongate tubular member 503. The first elongate tubular member 301 may also be adhesively fixed within the second lumen 508 of the second elongate tubular member 503.

A second arm or end 526 of the adaptor 521 is provided with a chamber 527 having proximal and distal ends 528 and 529. As shown in FIG. 33, the proximal extremity 504 of the second elongate tubular member 503 is adhesively secured within the distal end 529 of the chamber 527 in an appropriate manner so that a fluid tight seal is formed and the first lumen 507 of the second elongate tubular member 503 is aligned with the chamber 527 of the second arm 526 of the adaptor 521. This may be accomplished by severing and removing a portion of the proximal extremity 504 of the second elongate tubular member 503 carrying the second lumen 508 so that only the portion of the proximal extremity 504 of the second elongate tubular member 503 carrying the first lumen 507 may be secured within the chamber 527 of the second arm 526 of the adaptor 521.

As shown in FIG. 33, a loading chamber or casing 536 formed of an appropriate material, preferably PEBAX™ 72 D clear having an inner diameter greater than the outer diameter of the portion of the proximal extremity 504 of the second elongate tubular member 503 carrying the first lumen and, preferably, approximately 0.045", is adhesively secured within the chamber 527 of the second arm 526 of the adaptor 521 so that, proximally, the casing 536 extends out of the second arm 526 and distally, it receives the same portion of the proximal extremity 504 of the second elongate tubular member 503 as it enters the distal end 529 of the chamber 527 in the adaptor 521.

Alternatively, the chamber 527 of the adaptor 521 may be provided with a second arm 526 having a tapered proximal end 528 as hereinafter described.

A capsule or casing 541 for containing and compressing the solid biological sealant 542 is provided and is constructed of a suitable plastic material such as PEBAX™, Elf Atochem™ or other suitable thermoplastic elastomer having a shore hardness durometer of 72 D. The capsule 541 is sized so as to be capable of being introduced into and retained in the casing 536 in the proximal end 528 of the chamber 527 in the second arm 526 of the adaptor 521 so that the solid biological agent 542 can be extruded out of said capsule 541 and adaptor 521 and into the first lumen 507 of the second elongate tubular member 503 as hereinafter described. Thus, the capsule 541 has a suitable length ranging from 0.5", to 2", preferably 1.5", an outer diameter greater than the outer diameter of the second elongate tubular member 503 and less than the inner diameter of the loading chamber 536 and an internal diameter being smaller than the internal diameter of the first lumen 507 of the second elongate tubular member 503, ranging from 0.015" to 0.055", preferably being 0.036".

The capsule 541 is loaded with solid sealant 542 prior to being introduced into the device 501. The sealant 542 is compressed and centered in the capsule 541 so that the capsule 541 extends several millimeters beyond the compressed sealant 542 at either end thereof.

As hereinafter described, the solid biological sealing agent 542 is extruded out of the capsule 541 and adapter 521 and into the first lumen 507 of the second elongate tubular member 503 by the use of a sealant placement member 561 having proximal and distal extremities 562 and 563 and a proximal hub, cap or handle 564. The placement member 561 may be in the form of a push rod or a push wire constructed of an appropriate flexible plastic or metal material.

The placement member 561 has a suitable diameter so that it is capable of being slidably disposed in the casing 536, capsule 541, adaptor 521 and first lumen 507 of the second elongate tubular member 503 as hereinafter described. The cap 564 of the sealant member 561 is constructed of an appropriate material such as Polycarb™ and is adhesively secured to the proximal extremity 562 thereof so as to prevent the sealant placement member 561 from extending distally out of the first lumen 507 of the second elongate tubular member 503 and into the artery 107 as hereinafter described. The sealant placement member 561 has a suitable length so that when fully inserted and disposed in the first lumen 507 of the second elongate tubular member 503 the hub 564 abuts or is seated against the casing 536 in the proximal chamber 528 of the adaptor 521, thus functioning as a backstop, and the distal extremity 563 of the sealant placement member 561 terminates at or several millimeters distal of the end of the first lumen 507 of the second elongate tubular member 503.

Operation and use of the device 501 is similar to that described for the expansile device 301 except for the sealant introducer means in the device 501. As soon as it has been established that a good seal has been formed between the occlusion assembly 307 and the wall 103 adjacent the puncture the physician can introduce the solid sealant as hereinafter described and shown in FIG. 34A–C.

The sealant containing capsule 541 can be loaded into the device 501 as hereinbefore described prior to the device 501 being placed into the patient or after a good seal has been established therewith. In addition, multiple capsules may be provided during sterile packaging of the device 501 permitting the physician to deploy as much sealant as is necessary to seal a puncture.

While holding the handle 564 of sealant placement member 561, the physician inserts the distal extremity 563 thereof into the capsule 541 retained in the casing 536 in the chamber 527 of the second arm 526 of the adaptor 526. Pushing the placement member 561 in a distalward direction extrudes the sealant 542 out of the capsule 541, with the capsule 541 being retained in the casing 536, and out of the adaptor 521 into the first lumen 507 of the second elongate tubular member 503. Continued distal movement of the placement member 561, until the hub 564 thereof seats against the capsule 541, advances the compressed sealant 542 distally in the first lumen 507 and out of the first lumen 507 into the body proximal to the expansile member 309 and external to the lumen 104 of the vessel 107. The bevel on the tip 509 of the second elongate tubular member 503 permits easy, accurate and effective placement of the solid sealant 542 without buckling or folding of the same as shown in FIG. 34A–C.

The remainder of the operation of the device 501 is as hereinbefore described in conjunction with use of the device 301. Thus, the use of device 501 is also compatible with use of the tensioning device 335 as hereinbefore described.

Another embodiment of an expansile device incorporating the present invention is shown in FIGS. 35–36. The expansile device 601 is similar to that shown in FIG. 33 with the principal difference being in the biological sealant introduction means utilized in the device 601. Thus, all the parts of the expansile device 501 that are present in the expansile device 601 carry the same numbers. Solid biological sealant introducer means 602 is similar to the introducer means 502 shown in FIG. 33 with the principal difference being that the first elongate tubular member 302 is not fixed in relation to the second elongate tubular member 503. Rather, the second elongate tubular member 503 is slidably carried by the first elongate tubular member 302 as hereinafter described.

The second elongate tubular member 503 in device 601 is similar in construction to that in device 501 with the principal difference being that the second lumen is absent in device 601.

The second elongate tubular member 503 carries at least one, but, preferably, proximal and distal external eyes, rails or rings 603 and 604, said first elongate tubular member 302 being slidably disposed in said external eyes 603 and 604 as hereinafter described. It should be appreciated that any appropriate number of external eyes or guides may be utilized. The external eyes 603 and 604 are formed of a suitable material such as extruded Pebax™ having a similar shore hardness and are appropriately bonded to the second elongate tubular member 503, by either being thermally or adhesively bonded thereto.

The external eyes 603 and 604 are of a suitable size, as for example having outer diameters ranging from 0.030–0.050" and inner diameters ranging from 0.010–0.045", but in no case having inner diameters smaller than the outside diameter of the first elongate tubular member 302 and the deployment means 308 carried thereby. The external eyes 603 and 604 have lengths ranging from 0.5–4 centimeters.

As shown in FIG. 35, the proximal eye 603 is carried at an appropriate position along the longitudinal axis of the second elongate tubular member 503 so that it can slide over, be guided by, and simultaneously support, the first elongate tubular member 302 as hereinafter described.

The distal eye 604 carries a soft beveled distal tip 611 constructed of an appropriate material such as Pebax™ having a shore hardness durometer less than that of the distal eye 604, preferably approximately 90 A. The tip 611 is thermally or adhesively bonded to the distal eye 604. As shown in FIG. 35, the distal eye 604 and tip 611 carried thereby are bonded to the distal extremity 506 of the second elongate tubular member 503 so that the bevel of the tip 611 and the bevel of the tip 509 of the distal extremity 506 of the second elongate tubular member 503 are contiguous and lie in the same plane, the tip 611 of the distal eye 604 thus extending distal to the tip 509 of the distal extremity 506 of the second elongate tubular member 503. The softer, distally extending tip 611 of the distal eye 604 provides for easier and smoother sliding of the second elongate tubular member 503 over the first flexible elongate tubular member 302 as hereinafter described.

It should be appreciated that the external eyes can also be constructed by starting with an extruded catheter material similar to that utilized for the device 501 and subsequently removing all of the catheter portion carrying the second lumen except for predetermined lengths thereof which form said eyes.

As shown in FIG. 35, proximal adaption for solid sealant introduction into the lumen 507 of the second elongate tubular member is similar to that described in conjunction with the device 501 except for that fact that the proximal hub or adaptor 521 of device 601 is provided with a single end or arm 526. Thus, as hereinafter described, when the first flexible elongate tubular member 302 is disposed in the external eyes 603 and 604 the deployment means 308 of the proximal extremity 303 of the first flexible elongate tubular member 302 are exposed and freely operative as hereinbefore described.

Operation and use of the device 601 is similar to that described for the expansile device 501 except as hereinafter described and shown in FIG. 36A–C. The first flexible elongate tubular member 302 carrying the expansile assembly 307 may be used initially with or without the second elongate tubular member 503 and the solid sealant introduction means 602 carried thereby. If used separately, as soon as it has been established that a good seal has been formed between the occlusion assembly 307 and the wall 103 adjacent the puncture and all other sheaths are removed the physician can introduce the solid sealant as hereinafter described.

While manually maintaining proximal tension on the first flexible elongate tubular member 302 the proximal extremity 303 thereof, carrying the deployment means 308, is threaded distally to proximally through the tip 611 of the distal eye 604 and the proximal eye 603 of the second elongate tubular member 503. The second elongate tubular member 503 is pushed distally, guided by and sliding along the first flexible elongate tubular member 302 until the tip 611 of the distal eye 604 rests or abuts up against the proximal end of the hypotube 328 carried by the distal extremity 304 of the first flexible elongate tubular member 302.

When the second elongate tubular member 503 is positioned as hereinbefore described, the tensioning device 335 may be applied to the first flexible elongate tubular member 302. As shown in FIG. 36A–C, this is accomplished by gently bending a portion of the second elongate tubular member 503 laterally so that the grasping members 351 of the grasping arms 352 of the tensioning device 335 are placed around and grasp the first flexible elongate tubular member 302 only.

The remainder of the operation of the device 601 is as hereinbefore described in conjunction with use of the device 501.

It should be appreciated that other embodiments of the present invention are contemplated. For example, in one embodiment, a substantially coaxial arrangement of first and second elongate tubular members is provided in which the first member is slidably disposed within the lumen of the second member. Solid biological sealant is compressed and loaded or contained coaxially between first and second elongate tubular members at an predetermined appropriate position along the lengths thereof. Deployment of the expansile member is followed by proximal withdrawal of the second elongate tubular member, over and off of the first flexible elongate tubular member, which exposes the sealant to the tissue tract, external to the vessel wall and adjacent to the expansile member.

It is apparent from the foregoing that there has been provided an expansile or closure device and method for percutaneous access and occlusion of punctures which medical procedures have required being placed in the human body. By varying the free shape or configuration of the super elastic alloy expansile member and the size and material of the membrane, the predetermined configuration and rigidity of the expansile assembly is varied so that it becomes possible to occlude puncture sites and natural tracts of various sizes and in various locations in the body such as laparoscopic puncture sites, pleural-cutaneous fistulas, including chest-tube puncture sites, intestinal-cutaneous fistulas, fistulas between the intestines, biliary tract of the stomach and the like. The expansile assembly establishes the distal boundary for the puncture so that it enables accurate placement of and prevents inadvertent intravascular injection and embolization of the biological sealant. The expansile device of the present invention makes possible the use of biological sealants in which for example fibrin glue is utilized and forms a clot which has greater strength than a natural clot formed by the body. In addition it makes it possible to the bypass the natural coagulation system of the human body even though anticoagulants have been administered to the patient during the prior medical procedure or procedures. Although fibrin glue has been discussed as the principal biological sealant, other sealants may be utilized such as collagen, Avitene™ slurries, Gel Foam™, cellulose, fibrin and thrombin, collagen and thrombin mixtures, all of which are non-adherent to the expansile device. Individual components of multi-component sealants may be separately introduced into the different annular spaces of the expansile device comprising three flexible elongate tubular members. By utilizing an annular distal mixing chamber, component-to-component fluid contact is maximized. A maximized area of contact affords optimal mixing and setting of the sealant at just the site where it is needed. Furthermore, circumferential introduction of mixed biological sealant into the puncture provides better distribution. In addition, it should be appreciated that other means of sealant introduction to the flexible elongate tubular member are available. For example, a multi-component sealant such as fibrin glue may, alternatively, be mixed prior to introduction into the flexible elongate tubular member.

Solid biological sealants may also be used, such as collagen plugs compressed and contained or retained in casings or capsules, which are capable of being introduced into and extruded from the expansile device and placed external to the vessel wall. Solid sealant introduction means are provided which do not require additional tissue tract dilation or trauma in order to accurately place solid sealant external and adjacent to the puncture in the vessel wall. Such auto-placement or auto-positioning assures accurate deposition of solid sealant with a minimum of additional procedural steps and obviates the problem of solid sealant buckling or folding as the same is advanced into position. In addition, the decision to use such introduction means may be made after the expansile member is already in place within the vessel. In such situations, solid sealant introduction means may be placed over an expansile device not initially carrying such means.

The shape of the expansile mechanism utilized in the expansile device of the present invention that abuts the inner surface of the wall through which the puncture extends enlists the normal pressure of the arterial blood flow to help retain the expansile assembly in contact with the wall. The expansile assembly is small in size and even when being deployed into the blood vessel permits substantially unobstructed blood flow through the vessel to continue during the expansile procedure thus avoiding ischemic and thrombotic complications associated with stasis of blood. The small size similarly prevents the expansile assembly from damaging or impinging on the opposite wall of the blood vessel during deployment or de-deployment of the device.

Since the expansile device and method of the present invention does not require long term intravascular deployment of a foreign body such as collagen, intra-arterial anchors or sutures, nor does it utilize balloon technology with the attendant risks of balloon rupture or tearing, there is a greatly reduced risk of life and limb threatening infections and the introduction of particulates or air emboli into the bloodstream.

The catheter retention and tension applicator of the present invention provide a constant force of proximal tension on the deployed device. An inherent safety feature is the constant force of tension provided over a range of motion as hereinbefore discussed. As this obviates the need for manual pressure and clamping devices traditionally used, it frees medical personnel to attend to other duties.

Since the occlusions which are formed in punctures utilizing the expansile device and method of the present invention can be accomplished quickly, this facilitates early ambulation of the patient and helps to avoid traditional complications such as arterio-venous fistulas, pseudo-aneurysms, thrombosis and embolism. Since the device is typically disposed of after one use, the danger of transmitting diseases to the blood stream of the patient is greatly reduced. Medical costs to the patient and to society are also thereby reduced.

Although the expansile device and method have been described principally in use with the human body it should be appreciated that the expansile device and method also can be utilized with animals in a similar manner.

In addition, it should be appreciated that the expansile device can be used within other natural tracts in the body in order to provide for other therapeutic or prophylactic modalities.

It is apparent from the foregoing that there has been provided a expansile device and method for percutaneous access and occlusion of puncture sites in the human body that have distinct advantages over those heretofore provided.

As hereinbefore described, it should also be appreciated that the process for making the Gelfoam slurry biological sealant and the sealant system or, simply, the Gelfoam slurry hereinbefore described can be utilized in conjunction with other vascular closure devices. One such device is designated by the trademark PROSTAR and is marketed by Perclose, Inc. of Menlo Park, Calif. By the use of percutaneously inserted needles secured to sutures 721, the device percutaneously sutures a puncture 106 in a blood vessel wall 103 thereby occluding the puncture 106. The sutures 721 are tied and the tails 722 thereof extend proximally, out of the tissue tract 106 created at the time of the vascular access procedure and thence out of the body. It has been determined that in spite of using the PROSTAR device to seal a puncture, there is often continued bleeding from the puncture. It is, therefore, advantageous to supplement such a closure with gelatin slurry biological sealant. Accordingly, a Gelfoam slurry biological sealant system is provided as hereinbefore described. Use of the system in conjunction with the PROSTAR is as hereinafter described and shown in FIGS. 39A–C. The tails 722 of the sutures 721 extending proximally out of the body are threaded through the slot 702 in the distal end of the insertion catheter 701 and into the lumen 704 of the catheter 701 by applying pressure on the bevel 703 of the distal slot 702 with the tails 722. The tails 722 are then pulled proximally until they catch and become disposed in the eye 706 of the slot 702, exiting the lumen 704 of the injection catheter 701 thereat as shown in FIG. 39. The distal end of the injection catheter 701 is carefully advanced over the sutures 721 distally into and down the tissue tract 106 associated with the sutured puncture 106 until it is adjacent the vessel wall 103 and sutures 721. After blending the Gelfoam slurry sealant 723, the sealant 723 in the syringe 724 is sterilely deposited into the injection catheter 701, in which the suture tails 722 are partially disposed, as the catheter 701 is withdrawn, thus introducing the sealant 723 into the tract 106 proximal to the wall 103 of the blood vessel 107 and adjacent the tied sutures 721.

The sealant 723 is then permitted to facilitate hemostasis for a predetermined period of time as hereinbefore described. Thereafter, the sealant 723 may be retained in the tissue tract 106, wherefrom it is reabsorbed over a period of time, or it may be removed therefrom. The remainder of the procedure is as hereinbefore described.

Another vascular closure device with which the Gelfoam slurry sealant, system and method may be utilized is designated by the trademark ANGIOSEAL, marketed by Sherwood, Davis and Geck of St. Louis, Mo. The device uses an introducer sheath to place an absorbable anchor 731 into the vessel 107 through the puncture 106 therein. The anchor 731 carries at least one, usually two, sutures 732 secured thereto, the sutures 732 being adapted to extend from the puncture 106 to outside the body along the tissue tract 106 associated therewith. During deployment, after the anchor 731 is placed intravascularly but before the sheath is removed from the tissue tract 106, a collagen plug 733 or sponge with a hole or lumen which has been threaded over the sutures 732 and engaged thereby is also deposited into the tissue tract 106. The suture 732 is adapted to be pulled proximally by the operator in order to pull the anchor 731 proximally into engagement with the wall 103 in the lumen 104 of the blood vessel 107 whereupon the sutures 732 are ligated over the collagen plug 733. Ligation pulls the collagen plug 733 distally so that it becomes firmly disposed adjacent the outer wall 103 of the vessel 107 and the sutures 732 thereby substantially occluding the puncture 106. As shown in FIGS. 40A–C, the remainder of the method of introducing the Gelfoam slurry sealant 723 is as hereinbefore described in conjunction with the PROSTAR device.

Another vascular closure device with which the Gelfoam slurry sealant, system and method may be utilized is designated by the trademark VASCULAR SOLUTIONS DUETT and is marketed by Vascular Solutions of Minneapolis, Minn. The device is inserted through a conventional sheath introducer carrying a sidearm and comprises an elongate tubular member having proximal and distal extremities, the distal extremity being sized so that it is adapted to extend through the puncture in the wall into the lumen of the blood vessel, an inflatable member carried by the distal extremity and movable between deflated and inflated positions and deployment means carried by the proximal extremity of the elongate tubular member and adapted to be operated by the human hand for controlling movement of the inflatable member between deflated and inflated positions by the introduction of liquid or air thereto. The method of use of the device and gelatin slurry sealant is as hereinbefore described in conjunction with the vascular closure device of the present invention with the exception that the Gelfoam slurry is introduced through the sidearm of the sheath introducer after the device has been deployed and the distal end of the sheath has been withdrawn proximally out of the vessel.

A variation of the VASCULAR SOLUTIONS DUETT device carries a sealant injection lumen. Use of this device with the gelatin slurry of the present invention is as hereinbefore described in conjunction with the closure device of the present invention.

Another vascular closure device with which the Gelfoam slurry sealant, system and method may be utilized is designated by the trademark VASOSEAL and is marketed by Datascope. As shown in FIG. 41A–E, the device comprises an insertion sheath 751 adapted to be passed distally through a tissue tract 106 until it is adjacent the puncture 106 outside the wall 103 of the vessel 107, a mass of hemostatic material 752, such as a collagen plug, adapted to be disposed in said insertion sheath 751 and means 753 for advancing said hemostatic material 752 distally out of said sheath 751 when said sheath 751 is pulled proximally while manual pressure 754 is maintained on the vessel 107 distal to the puncture 106 so that said hemostatic material 752 is deposited adjacent the puncture 106 outside the wall 103 of the vessel 107 thereby occluding the puncture 106. As shown in FIGS. 41A–E, the Gelfoam slurry sealant 723, and system for making the same, can be utilized in conjunction with this device by blending the slurry 723 and introducing it into the introducer 751, as hereinbefore described, prior to placing the hemostatic material 752 into the introducer 751.

A variation of the aforementioned devices includes a system marketed by Kensey Nash Corporation of Exton, Pa. This system comprises the use of the PROSTAR device followed by the insertion of a hemostatic plug which is formed with a lumen through which the suture tails can be extended so that, subsequently, the plug can be threaded distally into the tissue tract in a manner similar to that hereinbefore discussed. It should be appreciated that the Gelfoam slurry sealant, system and method of using is readily adaptable to this system.

As hereinbefore described, the system of the present invention is also readily adaptable to be used in conjunction with other vascular closure devices.

Percutaneous methods are widespread techniques that offer less invasive, safer and more cost-effective diagnostic and therapeutic access to organs of the human body. In order to fully realize the advantages of percutaneous access however, morbidity associated with access sites must be anticipated and prevented wherever possible. Indeed, advanced therapeutic interventions have led to a greater range of access site complications. A patient who suffers such complications must often undergo a more invasive procedure in order to prevent devastating injury to life or limb. Such procedures incur additional risks and costs. Effective percutaneous occlusion of a percutaneous vascular access site that proves to be otherwise difficult to manage is a major achievement. Without such treatment many of the advantages of percutaneous diagnostic and therapeutic procedures are lost. Satisfactory solutions have heretofore been absent in the prior art. The device and method of the present invention obviate many of the morbid side effects associated with puncture sites hereinbefore described.

What is claimed:

1. A biological sealant comprising a gelatin slurry which includes milled gelatin powder.

2. A biological sealant as in claim 1 wherein said slurry includes Gelfoam (trademark) powder mixed with a diluent selected from the group consisting of saline and water.

3. A biological sealant as in claim 2 wherein said slurry includes gelatin in an amount ranging from 0.5–10 per cent by weight.

4. A biological sealant as in claim 3 further including thrombin.

5. A biological sealant as in claim 4 wherein said slurry includes thrombin in the amount ranging from 10–20,000 units per milliliter.

6. A biological sealant as in claim 4 further including calcium.

7. A biological sealant as in claim 6 wherein said slurry includes calcium ions in an amount ranging from 1–500 milli-moles per milliliter of liquid.

8. A process for making a biological sealant comprising the steps of weighing an amount of milled gelatin powder, mixing said amount of milled gelatin powder with saline in a ratio of 5–100 mg of milled gelatin powder per milliliter of saline and blending said milled gelatin powder and saline together until a homogeneous slurry is created.

9. The process of claim 8 further including the step of mixing thrombin powder with the milled gelatin powder and saline in the ratio of 1–20,000 units of thrombin powder per milliliter of saline and blending said thrombin powder with said milled gelatin powder and saline together until a homogeneous slurry is created.

10. The process of claim 9 wherein the gelatin powder used is Gelfoam (trademark) powder.

11. The process of claim 10 further including the step of adding 1–10 millimoles of calcium ion per milliliter of saline to said gelatin powder, saline and thrombin powder.

12. A biological sealant system comprising milled gelatin powder and means for mixing said powder into a gelatin slurry.

13. A biological sealant as in claim 12 wherein said slurry includes gelatin in an amount ranging from 0.5–10 per cent by weight.

14. A biological sealant system as in claim 13 wherein said gelatin includes Gelfoam (trademark) and the slurry further includes thrombin.

15. A biological sealant system as in claim 14 wherein said slurry includes thrombin in the amount ranging from 1–20,000 units per milliliter.

16. A method for percutaneously forming a closure of a puncture in a wall of a blood vessel in the body, the blood vessel having a lumen defined by the wall, by use of a closure device having an expansion assembly movable between contracted and expanded positions and deployment means for controlling movement of the expansion assembly between contracted and expanded positions and a biological sealant comprising a gelatin slurry, said slurry including milled gelatin powder, the method comprising the steps of introducing the expansion assembly through the puncture into the lumen of the blood vessel, moving the expansion assembly from a contracted position to an expanded position, pulling the expansion assembly into engagement with the wall of the lumen of the vessel, introducing said biological sealant into the body proximal to the wall of the blood vessel and adjacent to the expansion assembly, permitting said biological sealant to assist hemostasis for a predetermined amount of time, thereafter moving the expansion assembly from the expanded position to the contracted position and removing the closure device from the biological sealant.

17. A method as in claim 16 further including the step of adding thrombin to said biological sealant prior to introducing the sealant into the body.

18. A biological sealant system for percutaneously forming a closure of a puncture in a wall of a blood vessel in the body, the blood vessel having a lumen defined by the wall, the system comprising a closure device having an expansion assembly movable between contracted and expanded positions, the expansion assembly in the contracted position being adapted to extend through the puncture in the wall deployment means adapted to be operated by the human hand for controlling movement of the expansion assembly between contracted and expanded positions, a predetermined quantity of milled gelatin powder, a predetermined quantity of thrombin powder and a predetermined quantity of saline.

19. A system as in claim 18 wherein said gelatin powder includes Gelfoam (trademark) and further including means for mixing said gelatin powder, thrombin powder and saline into a gelatin slurry and means for introducing said slurry into the body proximal to the wall of the blood vessel and adjacent to the expansion assembly.

20. A system as in claim 19 wherein said gelatin slurry introducing means includes a syringe.

21. A biological sealant system for percutaneously forming a closure of a puncture in a wall of a blood vessel in the body, the blood vessel having a lumen defined by the wall, the system comprising a closure device having at least one suture adapted to substantially occlude the puncture and to extend from the puncture to outside the body along a tissue tract, a predetermined quantity of milled gelatin powder, a predetermined quantity of thrombin powder and a predetermined quantity of saline.

22. A system as in claim 21 wherein said gelatin powder includes Gelfoam (trademark) and further including means for mixing said gelatin powder, thrombin powder and saline into a gelatin slurry and means for introducing said slurry into the body into said tissue tract proximal to the wall of the blood vessel and adjacent to the suture.

23. A system as in claim 22 wherein said gelatin slurry introducing means includes a syringe and an injection catheter having a slit therein.

24. A method for percutaneously forming a closure of a puncture in a wall of a blood vessel in the body, the blood vessel having a lumen defined by the wall, by use of a closure device having at least one suture adapted to extend from the puncture to outside the body along a tissue tract and a biological sealant comprising a gelatin slurry, said slurry including milled gelatin powder and thrombin, the method comprising the steps of suturing the puncture in the wall of the blood vessel with the suture, introducing said biological sealant into the body proximal to the wall of the blood vessel and into said tissue tract adjacent said suture and permitting said biological sealant to assist hemostasis for a predetermined amount of time.

25. A biological sealant system for percutaneously forming a closure of a puncture in a wall of a blood vessel in the body, the blood vessel having a lumen defined by the wall, the system comprising a closure device having an inflatable member movable between deflated and inflated positions, said inflatable member in the deflated position being sized so that it is adapted to extend through the puncture in the wall, deployment means carried by the device and adapted to be operated by the human hand for controlling movement of the inflatable member between deflated and inflated positions, a predetermined quantity of milled gelatin powder, a predetermined quantity of thrombin powder and a predetermined quantity of saline.

26. A system as in claim 25 wherein said gelatin powder includes Gelfoam (trademark) powder and further including means for mixing said gelatin powder, thrombin powder and saline into a gelatin slurry and means for introducing said slurry into the body proximal to the wall of the blood vessel and adjacent to the inflatable member.

27. A system in claim 26 wherein said gelatin slurry introducing means includes an injection catheter and a syringe.

28. A method for percutaneously forming a closure of a puncture in a wall of a blood vessel in the body, the blood vessel having a lumen defined by the wall, by use of a closure device having an inflatable member movable between deflated and inflated positions and a biological sealant comprising a gelatin slurry, said slurry including milled gelatin powder and thrombin, the method comprising the steps of introducing the inflatable member through the puncture into the lumen of the blood vessel, moving the inflatable member from a deflated position to an inflated position, pulling the inflatable member into engagement with the wall of the lumen of the vessel, introducing said biological sealant into the body proximal to the wall of the blood vessel and adjacent to the inflatable member, permitting said biological sealant to assist hemostasis for a predetermined amount of time, thereafter moving the inflatable member from the inflated position to the deflated position and removing the closure device from the biological sealant.

29. A biological sealant system for percutaneously forming a closure of a puncture in a wall of a blood vessel in the body, the blood vessel having a lumen defined by the wall, the system comprising a closure device having an anchor adapted to be placed through the puncture into the vessel, at least one suture secured to said anchor and a hemostatic plug engaging said suture, the suture adapted to extend from the puncture to outside the body along a tissue tract and to be pulled by the human hand in order to pull the anchor proximally and the hemostatic plug distally in order for said anchor and plug to engage the wall of the blood vessel to substantially occlude the puncture, a predetermined quantity of milled gelatin powder, a predetermined quantity of thrombin powder and a predetermined quantity of saline.

30. A system as in claim 29 wherein said gelatin powder includes Gelfoam (trademark) and further including means for mixing said gelatin powder, thrombin powder and saline into a gelatin slurry and means for introducing said slurry into the body proximal to the wall of the blood vessel and adjacent to the suture.

31. A system as in claim 30 wherein said gelatin slurry introducing means includes an injection catheter having a slit therein and syringe.

32. A method for percutaneously forming a closure of a puncture in a wall of a blood vessel in the body, the blood vessel having a lumen defined by the wall, by use of a closure device having an anchor, at least one suture secured to said anchor, a hemostatic plug engaging said suture and a biological sealant comprising a gelatin slurry, said slurry including milled gelatin powder and thrombin, the method comprising the steps of placing the anchor through the puncture into the vessel, pulling the suture proximally until the anchor and the hemostatic plug engage the wall of the vessel, introducing said biological sealant into the body proximal to the wall of the blood vessel and into said tissue tract adjacent said suture and permitting said biological sealant to assist hemostasis for a predetermined amount of time.

33. A biological sealant system for percutaneously forming a closure of a puncture in a wall of a blood vessel in the body, the blood vessel having a lumen defined by the wall, the system comprising a closure device having an insertion sheath adapted to be passed distally through a tissue tract until it is adjacent the puncture outside the wall of the vessel, a mass of hemostatic material adapted to be disposed in said insertion sheath and means for advancing said hemostatic material distally out of said sheath when said sheath is pulled proximally so that said hemostatic material is deposited adjacent the puncture outside the wall of the vessel a predetermined quantity of milled gelatin powder, a predetermined quantity of thrombin powder and a predetermined quantity of saline.

34. A system as in claim 33 wherein said gelatin powder includes Gelfoam (trademark) and further including means for mixing said gelatin powder, thrombin powder and saline into a gelatin slurry and means for introducing said slurry into the body proximal to the wall of the blood vessel.

35. A system as in claim 34 wherein said slurry introducing means includes an injection catheter and a syringe.

36. A method for percutaneously forming a closure of a puncture in a wall of a blood vessel in the body, the blood vessel having a lumen defined by the wall, by use of a closure device having an insertion sheath, a mass of hemostatic material adapted to be disposed in said insertion sheath and a biological sealant comprising a gelatin slurry, said slurry including milled gelatin powder and thrombin, the method comprising the steps of passing said insertion sheath distally through a tissue tract until is disposed adjacent the puncture outside the wall of the vessel, introducing said biological sealant into the insertion sheath distally so that it flows distally in the sheath and is deposited adjacent the puncture outside the wall of the vessel thereby sealing the puncture, inserting said mass of hemostatic material into the insertion sheath and advancing said hemostatic material distally in said sheath, pulling said sheath proximally while further advancing said hemostatic material distally out of said sheath so that said hemostatic material is deposited adjacent the puncture outside of the wall of the vessel and adjacent to said biological sealant and removing the sheath after a predetermined period of time.

37. A method for forming a closure of a puncture in a wall of a blood vessel in the body, the blood vessel having a lumen defined by the wall, by use of a gelatin slurry which includes milled gelatin powder, the method comprising the steps of introducing said gelatin slurry into the body proximal to the wall of the blood vessel and permitting said slurry to assist hemostasis for a predetermined period of time.

38. A method as in claim 37 further including the step of occluding the puncture in the wall of the blood vessel prior to the introducing step.

39. A method as in claim 37 further including the step of adding a predetermined quantity of thrombin to said slurry prior to the introducing step.

40. A method as in claim 38 further including the step of adding a predetermined quantity of calcium to said slurry prior to the introducing step.

41. A method as in claim 37 where the milled gelatin powder includes Gelfoam (trademark) powder.

42. A method for forming a closure of an opening in a wall of an organ in the body, the organ having an inside defined by the wall, by use a gelatin slurry which includes milled gelatin powder, the method comprising the steps of introducing said gelatin slurry into the body proximal to the wall of the organ and permitting said slurry to cure.

* * * * *